US011306326B2

(12) United States Patent
Lee et al.

(10) Patent No.: US 11,306,326 B2
(45) Date of Patent: Apr. 19, 2022

(54) BIOLOGICALLY ACTIVE SYNTHETIC NANOPARTICLE CONSTRUCTS AND METHODS OF USE THEREOF

(71) Applicant: Rutgers, The State University of New Jersey, New Brunswick, NJ (US)

(72) Inventors: Ki-Bum Lee, Monmouth Junction, NJ (US); Sahishnu Patel, Lake Hiawatha, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 339 days.

(21) Appl. No.: 16/437,898

(22) Filed: Jun. 11, 2019

(65) Prior Publication Data

US 2020/0181647 A1    Jun. 11, 2020

Related U.S. Application Data

(60) Continuation-in-part of application No. 16/102,876, filed on Aug. 14, 2018, now abandoned, which is a division of application No. 14/913,804, filed as application No. PCT/US2014/052569 on Aug. 25, 2014, now Pat. No. 10,100,332.

(60) Provisional application No. 61/947,898, filed on Mar. 4, 2014, provisional application No. 61/869,284, filed on Aug. 23, 2013.

(51) Int. Cl.
*C12N 15/87* (2006.01)
*A61K 47/69* (2017.01)
*B82Y 5/00* (2011.01)

(52) U.S. Cl.
CPC .......... *C12N 15/87* (2013.01); *A61K 47/6923* (2017.08); *B82Y 5/00* (2013.01); *C12N 2810/40* (2013.01)

(58) Field of Classification Search
None
See application file for complete search history.

(56) References Cited

U.S. PATENT DOCUMENTS

| | | | |
|---|---|---|---|
| 10,100,332 B2 * | 10/2018 | Lee | A61K 47/6923 |
| 2005/0176647 A1 | 8/2005 | Sugiyama et al. | |
| 2009/0047272 A1 | 2/2009 | Appelbaum et al. | |
| 2009/0208577 A1 | 8/2009 | Xu et al. | |
| 2010/0316702 A1 | 12/2010 | Briggs et al. | |
| 2012/0165957 A1 | 6/2012 | Everland et al. | |
| 2016/0302928 A1 | 10/2016 | Day et al. | |
| 2020/0390806 A1 | 12/2020 | Sharma et al. | |

FOREIGN PATENT DOCUMENTS

WO      2013/059831 A1    4/2013

OTHER PUBLICATIONS

Agbasi-Porter, Chiamaka et al., Transcription Inhibition Using Oligonucleotide-Modified Gold Nanoparticles, Bioconjugate Chemistry, vol. 17, No. 5, Sep. 1, 2006, pp. 1178-1183.
Extended European Search Report dated Jan. 31, 2017 in European Patent Application No. 14837321.0 (8 pages).
Liu, Yang et al., Delivery of Intact Transcription Factor by Using Self-Assembled Supramolecular Nanoparticles, Angewandte Chemie International Edition, vol. 50, No. 13, Mar. 21, 2011, pp. 3058-3062.
Patel, Sahishnu et al., NanoScript: A Nanoparticle-Based Artificial Transcription Factor for Effective Gene Regulation, ACS Nano, vol. 8, No. 9, Aug. 18, 2014, pp. 8959-8967.
Xiao, Xiangshu et al., A Cell-Permeable Synthetic Transcription Factor Mimic, Angewandte Chemie International Edition, vol. 46, No. 16, Apr. 13, 2007, pp. 2865-2868.
Timmers et al: "Nuclear and nucleolar localization of *Sacchromyces cerevisiae* Ribosomal proteins S22 and S25", FEBS Letters, 1999, vol. 452, pp. 335-340.
Ragin, et al: "Cellular Import Mediated by Nuclear Localization Signal Peptide Sequences" Chemistry & Biology, Aug. 2002, vol. 8, pp. 943-948.
Shah, et al.: "Guiding Stem Cell Differentiation into Oligodendrocytes using Graphene-Nanofiber Hybrid Scaffolds", Advanced Materials, Jun. 11, 2014, 26(22), pp. 1-15.
Chen, et al.: "Break-up of Two-Dimensional MnO2 Nanosheets Promotes Ultrasensitive pH-Triggered Theranostics of Dancer", Advanced Materials, Aug. 22, 2014, 26.41, pp. 1-8.
Li, et al.: "Biodegradable MnO2 Nanosheet-Mediated Signal Amplification in Living Cells Enables Sensitive Detection of Down-Regulated Intracellular MicroRNA", ACS Applied Materials & Interfaces, Jan. 26, 2017, 9,7, pp. 1-21.
Vang, et al.: "A Biodegradable Hybrid Inorganic Nanoscaffold for Advanced Stem Cell Therapy", Nature Communications, Aug. 8, 2018, vol. 9, pp. 1-14.
Dey, et al.: "Characterizing Molecular Adsorption on Biodegradable MnO Nanoscaffolds", The Journal of Physical Chemistry, Nov. 27, 2018, pp. 1-34.
Han, et al.: "MnO2 Nanorods Intercalating Graphene Oxide/ Polyaniline Ternary Composites for Robust High-Performance Supercapacitors", Scientific Reports, Apr. 28, 2014, 4 : 4824, DOI: 10.1038/srep04824, pp. 1-7.
Liu, et al.: "Electrostatic-Interaction-Assisted Construction of 3D Networks of Manganese Dioxide Nanosheets for Flexible High-Performance Solid-State Asymmetric Supercapacitors", ACS Nano, 2017,11, pp. 7879-7888, DOI 10.1021/acsnano.7b02344.
Nang, et al.: "Novel Multi-Drug Delivery Hydrogel Using Scar-Homing Liposomes Improves Spinal Cord Injury Repair", Theranostics, 2018; 8(16): pp. 4429-4446. doi: 10.7150/thno.26717.

(Continued)

*Primary Examiner* — Robert M Kelly
(74) *Attorney, Agent, or Firm* — Fox Rothschild LLP

(57) ABSTRACT

This application discloses the compositions comprising biologically active synthetic nanoparticle constructs and methods of use thereof to modify gene expression including transcriptional activation and transcriptional repression.

23 Claims, 8 Drawing Sheets

Specification includes a Sequence Listing.

(56) References Cited

OTHER PUBLICATIONS

Johnson, et al.: "Electrospun Fiber for Drug Delivery after Spinal Cord Injury and the Effects of Drug Incorporation on Fiber Properties", Cells Tissues Organs, 2015,16;202: pp. 116-135, DOI: 10.1159/000446621.

Lan, et al.: "Implantable Porous Gelatin Microspheres Sustained Release of bFGF and Improved its Neuroprotective Effect on Rats After Spinal Cord Injury", PLOS ONE, Mar. 14, 2017, pp. 1-16 [retrieved from internet: <<https://doi.org/10.1371/journal.pone.0173814>>].

* cited by examiner

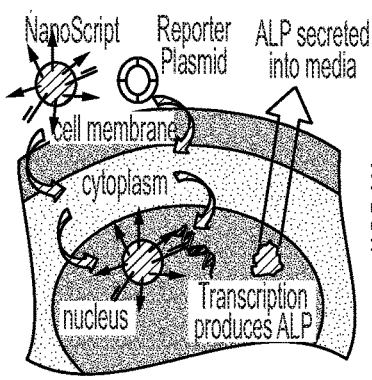
Figure 4(a)
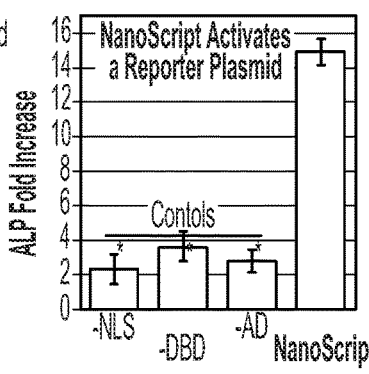
Figure 4(b)
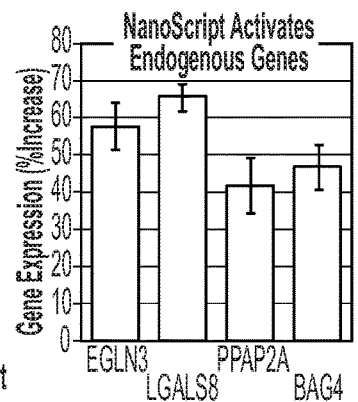
Figure 4(c)
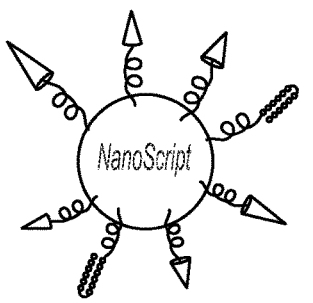
Figure 5(a)
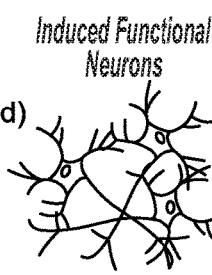
Figure 5(d)
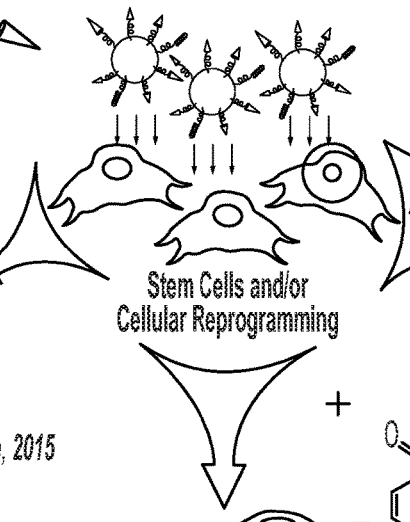
Figure 5(c)
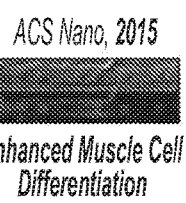
Figure 5(b)
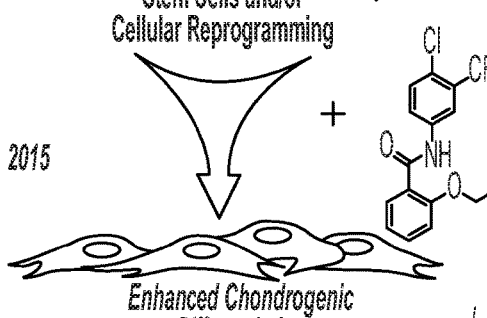

Figure 7(b)
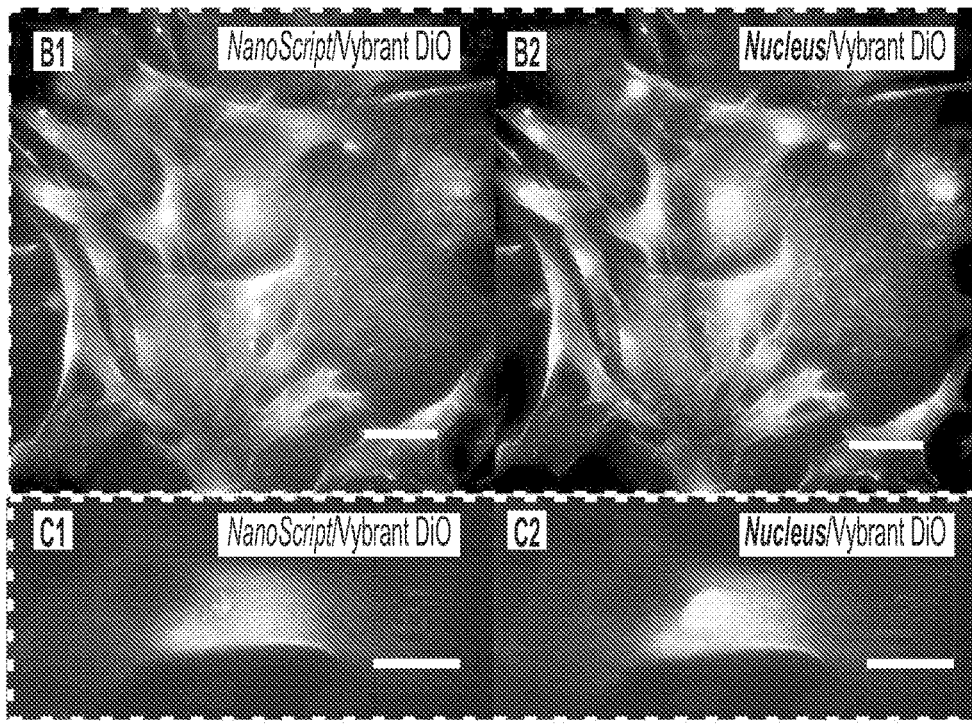
Figure 7(c)
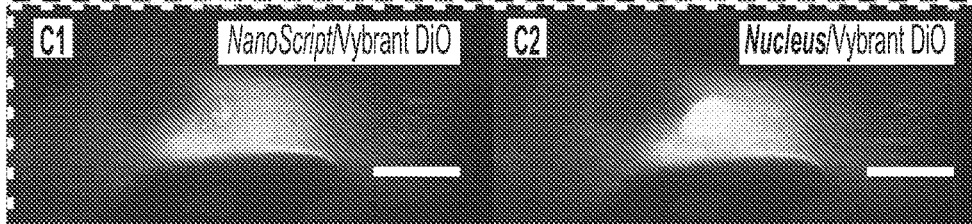
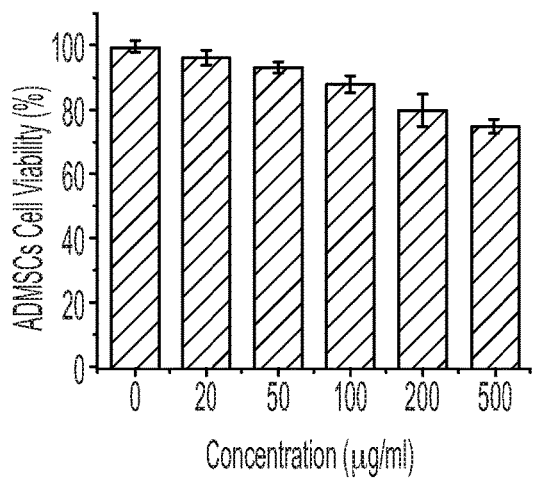
Figure 7(d)
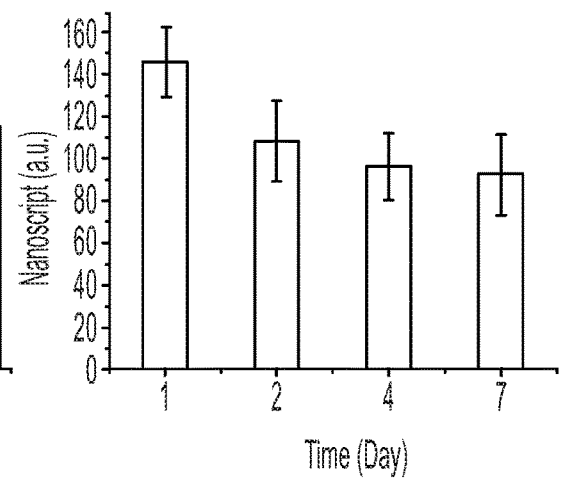
Figure 7(e)

SEQUENCE LISTING

<160> NUMBER OF SEQ ID NOS: 39

<210> SEQ ID NO 1
<211> LENGTH: 13
<212> TYPE: PRT
<213> ORGANISM: Human immunodeficiency virus type 1

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 18
<212> TYPE: PRT
<213> ORGANISM: Human immunodeficiency virus type 1

<400> SEQUENCE: 3

Lys Leu Ala Leu Lys Leu Ala Leu Lys Ala Leu Lys Ala Ala Leu Lys
1               5                   10                  15

Leu Ala

<210> SEQ ID NO 4
<211> LENGTH: 6
<212> TYPE: PRT
<213> ORGANISM: Artificial Sequence
<220> FEATURE:
<223> OTHER INFORMATION: chimeric sequence

<400> SEQUENCE: 4

Gly Trp Thr Leu Asn Ser
1               5

<210> SEQ ID NO 5
<211> LENGTH: 21
<212> TYPE: PRT
<213> ORGANISM: Artificial Sequence
<220> FEATURE:
<223> OTHER INFORMATION: chimeric sequence

<400> SEQUENCE: 5

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 6
<211> LENGTH: 17
<212> TYPE: PRT
<213> ORGANISM: herpes simplex virus 2

<400> SEQUENCE: 6

Asn Ala Lys Thr Arg Arg His Glu Arg Arg Arg Lys Leu Ala Ile Glu
1               5                   10                  15

Arg

<210> SEQ ID NO 7
<211> LENGTH: 17
<212> TYPE: PRT
<213> ORGANISM: Human immunodeficiency virus type 1

<400> SEQUENCE: 7

```
Gly Ala Leu Phe Leu Gly Phe Leu Gly Ala Ala Gly Ser Thr Met Gly
1               5                   10                  15
Ala

<210> SEQ ID NO 8
<211> LENGTH: 21
<212> TYPE: PRT
<213> ORGANISM: Artificial Sequence
<220> FEATURE:
<223> OTHER INFORMATION: synthetic sequence

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 18
<212> TYPE: PRT
<213> ORGANISM: Mus musculus

<400> SEQUENCE: 9

Leu Leu Ile Ile Leu Arg Arg Arg Ile Arg Lys Gln Ala His Ala His
1               5                   10                  15

Ser Lys

<210> SEQ ID NO 10
<211> LENGTH: 16
<212> TYPE: PRT
<213> ORGANISM: Artificial Sequence
<220> FEATURE:
<223> OTHER INFORMATION: synthetic sequence

<400> SEQUENCE: 10

Tyr Thr Ala Ile Ala Trp Val Lys Ala Phe Ile Arg Lys Leu Arg Lys
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: synthetic sequence

<400> SEQUENCE: 11

Ile Ala Trp Val Lys Ala Phe Ile Arg Lys Leu Arg Lys Gly Pro Leu
1               5                   10                  15

Gly

<210> SEQ ID NO 12
<211> LENGTH: 22
<212> TYPE: PRT
<213> ORGANISM: Artificial Sequence
<220> FEATURE:
<223> OTHER INFORMATION: synthetic sequence

<400> SEQUENCE: 12

Met Val Thr Val Leu Phe Arg Arg Leu Arg Ile Arg Arg Ala Cys Gly
1               5                   10                  15

Pro Pro Arg Val Arg Val
            20
```

```
<210> SEQ ID NO 13
<211> LENGTH: 20
<212> TYPE: PRT
<213> ORGANISM: Artificial Sequence
<220> FEATURE:
<223> OTHER INFORMATION: synthetic sequence

<400> SEQUENCE: 13

Gly Leu Trp Arg Ala Leu Trp Arg Leu Leu Arg Ser Leu Trp Arg Leu
1               5                   10                  15

Leu Trp Arg Ala
            20

<210> SEQ ID NO 14
<211> LENGTH: 29
<212> TYPE: PRT
<213> ORGANISM: Artificial Sequence
<220> FEATURE:
<223> OTHER INFORMATION: synthetic sequence

<400> SEQUENCE: 14

Ser Gly Leu Met Asp Leu Asp Phe Asp Asp Leu Ala Asp Ser Gly Leu
1               5                   10                  15

Met Asp Leu Asp Phe Asp Asp Leu Ala Asp Ser Gly Cys
            20                  25

<210> SEQ ID NO 15
<211> LENGTH: 4
<212> TYPE: PRT
<213> ORGANISM: Drosophila melanogaster

<400> SEQUENCE: 15

Trp Arg Pro Trp
1

<210> SEQ ID NO 16
<211> LENGTH: 19
<212> TYPE: PRT
<213> ORGANISM: Homo sapiens

<400> SEQUENCE: 16

Arg Leu Ile Thr Leu Ala Asp His Ile Cys Gln Ile Ile Thr Gln Asp
1               5                   10                  15

Phe Ala Arg

<210> SEQ ID NO 17
<211> LENGTH: 25
<212> TYPE: PRT
<213> ORGANISM: Artificial Sequence
<220> FEATURE:
<223> OTHER INFORMATION: synthetic sequence

<400> SEQUENCE: 17

Gln Ile Asn Asp Leu Tyr Ser Thr Asp Arg Pro Glu Ser Ala Glu Ala
1               5                   10                  15

Pro Asp Leu Gln Ser Trp Glu Leu Arg
            20                  25

<210> SEQ ID NO 18
<211> LENGTH: 27
<212> TYPE: PRT
<213> ORGANISM: Homo sapiens

<400> SEQUENCE: 18
```

Glu Leu Gln Lys Ser Ile Gly His Lys Pro Glu Pro Thr Glu Glu Trp
1               5                   10                  15

Glu Leu Ile Lys Thr Val Thr Glu Ala His Val
            20                  25

<210> SEQ ID NO 19
<211> LENGTH: 18
<212> TYPE: PRT
<213> ORGANISM: Drosophila melanogaster

<400> SEQUENCE: 19

Ser Thr Pro Ser Ser Lys Thr Lys Asp Leu Gly His Asn Asp Lys Lys
1               5                   10                  15

Ser Ser

<210> SEQ ID NO 20
<211> LENGTH: 29
<212> TYPE: PRT
<213> ORGANISM: Artificial Sequence
<220> FEATURE:
<223> OTHER INFORMATION: synthetic sequence

<400> SEQUENCE: 20

Cys Gly Ser Asp Ala Leu Asp Asp Phe Asp Leu Asp Met Leu Gly Ser
1               5                   10                  15

Asp Ala Leu Asp Asp Phe Asp Leu Asp Met Leu Gly Ser
            20                  25

<210> SEQ ID NO 21
<211> LENGTH: 13
<212> TYPE: PRT
<213> ORGANISM: Simian virus 40

<400> SEQUENCE: 21

Cys Gly Gly Gly Pro Lys Lys Lys Arg Lys Val Glu Asp
1               5                   10

<210> SEQ ID NO 22
<211> LENGTH: 6
<212> TYPE: DNA
<213> ORGANISM: Artificial Sequence
<220> FEATURE:
<223> OTHER INFORMATION: synthetic sequence

<400> SEQUENCE: 22 wgwwww                                                          6

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
cctatgacac gcctttcaaa aga                                       23

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
cagcaccata atcacgatct caa                                    23

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
attcgaaagg acctggagac cc                                     22

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
atcactgcta agcccaatgg c                                      21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ctgcggaccg aaagaagatg                                        20

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
atgcagcaac tcaaacagga t                                      21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
attctcgtca tcgtgtccgc                                        20

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
catccaggaa aggaaatctt gct                                    23

<210> SEQ ID NO 31
<211> LENGTH: 6

```
<212> TYPE: DNA
<213> ORGANISM: Artificial Sequence
<220> FEATURE:
<223> OTHER INFORMATION: synthetic sequence

<400> SEQUENCE: 31 tgttat                                                                  6

<210> SEQ ID NO 32
<211> LENGTH: 176
<212> TYPE: DNA
<213> ORGANISM: Photinus pyralis

<400> SEQUENCE: 32
gcggtaccgc tagcagctta taacattcca tatgttatac ataacattcc atatgttata       60
cataacattc catatgttat acgtcgacaa gctatgagat ctagactcta gagggtatat      120
aatggaagct cgactccagc ttggcattcc ggtactgttg gtaaaagctt cgaata          176

<210> SEQ ID NO 33
<211> LENGTH: 6
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: n is a, c, g, or t

<400> SEQUENCE: 33 canntg                                                                  6

<210> SEQ ID NO 34
<211> LENGTH: 16
<212> TYPE: PRT
<213> ORGANISM: Human immunodeficiency virus type 1

<400> SEQUENCE: 34

Cys Ala Leu Asn Asn Ala Gly Arg Lys Lys Arg Arg Gln Arg Arg Arg
1               5                   10                  15

<210> SEQ ID NO 35
<211> LENGTH: 5
<212> TYPE: PRT
<213> ORGANISM: Saccharomyces cerevisiae

<400> SEQUENCE: 35

Lys Ile Pro Ile Lys
1               5

<210> SEQ ID NO 36
<211> LENGTH: 7
<212> TYPE: PRT
<213> ORGANISM: Simian virus 40

<400> SEQUENCE: 36

Pro Lys Lys Lys Arg Lys Val
1               5

<210> SEQ ID NO 37
<211> LENGTH: 4
<212> TYPE: PRT
<213> ORGANISM: Artificial Sequence
<220> FEATURE:
<223> OTHER INFORMATION: synthetic sequence
```

```
<220> FEATURE:
<221> NAME/KEY: MISC_FEATURE
<222> LOCATION: (2)..(2)
<223> OTHER INFORMATION: Lys or Arg
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Lys or Arg

<400> SEQUENCE: 37

Lys Xaa Xaa Xaa
1

<210> SEQ ID NO 38
<211> LENGTH: 6
<212> TYPE: DNA
<213> ORGANISM: Artificial Sequence
<220> FEATURE:
<223> OTHER INFORMATION: synthetic sequence

<400> SEQUENCE: 38 ggtacc                                                                6

<210> SEQ ID NO 39
<211> LENGTH: 6
<212> TYPE: DNA
<213> ORGANISM: Artificial Sequence
<220> FEATURE:
<223> OTHER INFORMATION: synthetic sequence

<400> SEQUENCE: 39 aagctt                                                                6
```

BIOLOGICALLY ACTIVE SYNTHETIC NANOPARTICLE CONSTRUCTS AND METHODS OF USE THEREOF

CROSS REFERENCE TO RELATED APPLICATIONS

The present application is a continuation-in-part of U.S. Nonprovisional patent application Ser. No. 16/102,876 filed Aug. 14, 2018, now abandoned, which is a divisional of U.S. Nonprovisional Patent Application Ser. No. 14/913,804, filed Feb. 23, 2016, now issued as U.S. Patent No. 10,100,332, which is the U.S. National Phase of International Patent Application Serial No. PCT/US2014/052569 filed Aug. 25, 2014, which claims the benefit of priority under 35 U.S.C. § 119(e) of U.S. Provisional Application No. 61/869,284 filed Aug. 23, 2013 and U.S. Provisional Application No. 61/947,898 filed Mar. 4, 2014. The entire disclosures of the applications noted above are incorporated hereby reference.

STATEMENT REGARDING FEDERALLY SPONSORED RESEARCH

The invention described herein was supported in whole or in part by grants from the National Institutes of Health New Innovator Award No. NIH-1DP20D006462-01. The U.S. Government has certain rights in this invention.

FIELD OF THE INVENTION

This invention relates to biologically active synthetic nanoparticle construct compositions and methods of their use in regulating, mediating, or modifying biological activity and processes including gene expression and the cellular processes that rely on gene expression such as stem cell differentiation.

BACKGROUND OF THE INVENTION

Cellular biology comprises a wide range of study involving a broad set of cellular processes. These processes include, but are not necessarily limited to, cellular growth, maintenance, metabolism, proliferation, differentiation, migration, as well as inter- and intracellular signaling pathways. These cellular processes are mediated by a wide variety of endogenous proteins and other ligands, for example hormones and other steroids. While these cellular processes are incredibly varied, the regulation of these cellular processes can ultimately be traced back to regulation of gene expression, and most commonly, but not necessarily, regulation of gene expression at the transcriptional level.

Gene expression is the process wherein the information contained in a particular gene is ultimately manifested in a protein, the mechanism of which is explained by the Central Dogma Theory (CDT), which states that the flow of genetic information, under ordinary conditions, goes from DNA to RNA via transcription, and then from RNA to protein via translation. Since then, scientists have discovered several processes that are exceptions, notably for example that of reverse transcription such as that undertaken by retroviruses. Gene expression is most commonly regulated at the transcriptional level and involves the alteration of transcription rates within a cell. Transcriptional regulation may include either transcriptional activation or transcriptional repression. Transcription of a gene requires the presence of RNA polymerase (RNAP) to proceed. RNAP can initiate transcription at specific DNA sequences known as promoters. Transcriptional regulation often involves the use of transcription factors (TFs), which are compounds that can bind to specific DNA sequences. TFs can function as an activator and thus promote transcription, or a repressor, and thus block transcription. Activators bind to DNA regions known as enhancers, and enhance the interactions between RNAP and promoters, thus increasing the rate of transcription. Repressors bind to DNA regions known as silencers, and function to prevent the binding of RNAP to promoters, and thus prevent transcription.

TFs that function as activators include two fundamental domains that function synergistically to activate gene expression: the DNA-binding domain (DBD) and the activation domain (AD). The DBD targets and binds to specific enhancer DNA sequences, while the AD recruits proteins and RNAP to initiate and sustain transcription. TFs that function as repressors likewise include a DBD that similarly targets and binds to specific silencer DNA sequences. TFs that function as repressors may also include a repression domain (RD) and optionally non-DNA binding proteins called corepressors. In eukaryotes, corepressors are proteins that bind to certain repressors in order to activate them, so that the repressor can bind to the silencer region and block transcription.

The field of nanotechnology has recently made great strides in contributing to therapeutic applications ranging from molecular imaging, stem cell differentiation, and drug delivery. There have been past attempts to create synthetic analogues of TFs for use in a wide variety of therapeutic applications. These synthetic analogues are called synthetic transcription factors (STFs). Further, like endogenous TFs, STFs may act as either activators or repressors. Like TFs, STFs contain a DBD, and either an AD, if functioning as an activator, or an RD, if functioning as a repressor. Activator STFs have been developed in the past by combining a DBD moiety such as zinc finger, oligonucleotides, or hairpin polyamide, to an AD moiety such as wrenchnolol, peptoids, and peptides, to induce gene expression. Repressor STFs have been developed in the past by combining a DBD moiety with RD moieties to repress gene expression.

STFs possess a small molecular size, and have a high binding affinity for DNA, and they can exhibit specificity to bind to only certain sites, such as enhancers or silencers, for example via tunable hairpin polyamides that complement targeted DNA sequences. As such, STFs have significant potential therapeutic application. However, existing STFs suffer from a number of known problems that currently limit their potential therapeutic applications. STFs are known to have poor penetration of the nuclear membrane, which is significant because transcription occurs in the nucleus. STFs that cannot easily penetrate the nuclear membrane cannot effectively regulate transcription. Furthermore, STFs are often subject to intracellular degradation, thus limiting their effectiveness. Biologically active synthetic nanoparticle constructs having biologically inert substrates, such as gold nanoparticles, as the base platform upon which other elements of the biologically active synthetic nanoparticle construct are bound, are known. However, there remains a need for alternative base platforms for biologically active synthetic nanoparticle constructs that can overcome at least one of the above limitations, and provide effective compositions for use in regulating, mediating, or modifying biological activity and processes, including gene expression and the cellular processes that rely on gene expression such as cellular proliferation, differentiation, and migration. In particular, there is a need for alternative platforms that provide additional functionality.

SUMMARY OF THE INVENTION

The invention described herein involves biologically active synthetic nanoparticle constructs and methods of use of the biologically active synthetic nanoparticle constructs.

One aspect of the present invention provides a biologically active synthetic nanoparticle construct comprising a polypeptide-dendrimer nanoparticle, and a plurality of moieties attached to a surface of the polypeptide-dendrimer nanoparticle, wherein the moieties comprise: (i) a plurality of single copies of DNA binding domains, (ii) a plurality of single copies of nuclear localization signals, and (iii) a plurality of single copies of transcriptional domains; wherein the DNA binding domains are each individually covalently attached to the surface of the polypeptide-dendrimer nanoparticle, wherein the nuclear localization signals are each individually covalently attached to the surface of the polypeptide-dendrimer nanoparticle, and wherein the transcriptional domains are each individually covalently attached to the surface of the polypeptide-dendrimer nanoparticle.

In one embodiment of the invention (i) X % of the moieties on the polypeptide-dendrimer nanoparticle are DNA binding domains, wherein X % ranges from 10 to 70%; (ii) Y % of the moieties on the polypeptide-dendrimer nanoparticle are transcriptional repression domains, wherein Y % ranges from 10 to 70%; (iii) Z % of the moieties on the polypeptide-dendrimer nanoparticle are nuclear localization signals, wherein Z % ranges from 10 to 70%; and (iv) the sum of X, Y, and Z is not greater than 100%. In another embodiment, the moieties further comprise a plurality of at least one conjugant; wherein W % of the moieties on the polypeptide-dendrimer nanoparticle are the conjugants, wherein W % ranges from 0 to 40%; and wherein the sum of W, X, Y and Z % is not greater than 100%. In yet another embodiment, Z % is at least 50%. In a further embodiment, Z % is at least 60%.

In one embodiment, the polypeptide-dendrimer nanoparticle comprises (i) a hydrophobic core comprising a dendrimer, wherein the dendrimer comprises an amide linker and an amine functionalization suitable for N-carboxyanhydride polymerization; (ii) a hydrophobic inner shell comprising an inner shell polypeptide, wherein the hydrophobic inner shell at least partially surrounds the hydrophobic core; and (iii) a hydrophilic outer shell comprising an outer shell polypeptide, wherein the hydrophilic outer shell at least partially surrounds the hydrophobic inner shell. In another embodiment, the dendrimer comprises a polyamidoamine. In yet another embodiment, the hydrophobic core comprises a degradable nanomaterial, having multi-amine functionalization. In a further embodiment, the hydrophobic amino acids are selected from the group consisting of glycine, alanine, valine, leucine, isoleucine, phenylalanine, methionine, tryptophan, cysteine, and a combination thereof. In still a further embodiment, the outer shell polypeptide comprises polymerized alpha amino acids. In a different embodiment, the alpha amino acids are selected from the group consisting of lysine, glutamic acid, aspartic acid, and a combination thereof. In one embodiment, the outer shell polypeptide has an isoelectric point of from at least 6.5 to no more than 8. In another embodiment, the outer shell polypeptide has at least one functional group attached thereto. In yet another embodiment, the functional group is selected from the group consisting of an amine, carboxyl, phosphonate, sulfonate, and a combination thereof. In a further embodiment, the functional group consists of sulfosuccinimidyl 4-(N-maleimidomethyl)cyclohexane-1-carboxylate. In still a further embodiment, the functional group is suitable for bioconjugation. In a different embodiment, the bioconjugation occurs through a thiol-maleimide click reaction.

In one embodiment of the invention, the polypeptide-dendrimer nanoparticle has an outer diameter of no more than 30 nm. In another embodiment, the polypeptide-dendrimer nanoparticle outer diameter is controlled by the ratio of amino acid monomer to dendrimer.

In one embodiment of the invention, the polypeptide-dendrimer nanoparticle is loaded with at least one of, hydrophobic small molecules, oligonucleotides, and ions. In another embodiment, the ion is selected from the group consisting of gadolinium, manganese, rhenium, and a combination thereof.

In one embodiment of the invention, the polypeptide-dendrimer nanoparticle is prepared by the process of (i) performing a Michael addition and amidation reaction between an amine and an acrylate to form a hydrophobic dendrimer core having an outer surface; (ii) polymerizing a plurality of hydrophobic amino acids, by N-carboxyanhydride polymerization, in the presence of the hydrophobic dendrimer core, to form a hydrophobic polypeptide inner shell having an outer surface, wherein the hydrophobic polypeptide inner shell at least partially surrounds the outer surface of the hydrophobic core; and (iii) polymerizing a plurality of hydrophilic alpha amino acids, by N-carboxyanhydride polymerization, in the presence of the hydrophilic inner shell, to form a hydrophilic polypeptide outer shell having an outer surface, wherein the hydrophilic polypeptide outer shell at least partially surrounds the outer surface of the hydrophobic inner shell. In another embodiment, the amine comprises tri(2-aminoethyl)amine, and the acrylate comprises methyl acrylate.

In one embodiment of the invention, the DNA binding domain is selected from the group consisting of hairpin polyamides, zinc finger domains, triplex-forming oligonucleotides, transcription activator-like effectors, oligonucleotide analogs, locked-nucleic acids, peptide nucleic acids, and a combination thereof. In another embodiment, the DNA binding domains are hairpin polyamides comprising at least one N-methyl-imidazole moiety or at least one N-methyl pyrrole moiety, or combinations thereof, arranged sequentially on the polyamide to bind a target gene.

In another embodiment of the invention, the transcriptional domains are selected from the group consisting of transcriptional activation domains and transcriptional repression domains. In a further embodiment, the transcriptional activation domains are selected from the group consisting of peptoids, amphipathic isoxasolidine, wrenchnolol, amphipathic helix peptides and combinations thereof. In yet another embodiment, the transcriptional domains consist of peptides. In still a further embodiment, the peptides are in the D-isomer.

In one embodiment of the invention, the nuclear localization signals follow the Chelsky sequence. In another embodiment, the nuclear localization signals are non-classical. In yet another embodiment, the nuclear localization signals are derived from an SV-40 antigen, derived form an HIV-1 antigen, or derived from the group consisting of: TAT, Penetratin, MAP, Transportin/TP10, VP22, MPG, Pep1, pVEC, YTA2, YTA4, M918, CADY, and combinations thereof.

In one embodiment of the invention, the moieties are attached to the surface of the polypeptide dendrimer nanoparticle by crosslinking molecules.

In another embodiment of the invention, the biologically active nanoparticle construct binds to the DNA binding domains with an affinity having an equilibrium dissociation constant ($K_d$) of about 1 mM or less.

In yet another one embodiment of the invention, the ratio of DNA binding domains to nuclear localization signals to transcriptional domains is tunable.

In a further one embodiment of the invention, the biologically active synthetic nanoparticle construct is at least one of biodegradable or biocompatible.

BRIEF DESCRIPTION OF THE DRAWINGS

FIG. 3(a) Schematic diagram of a core-shell polypeptide nanoparticle structure, including a hydrophobic poly(amidoamine) (PAMAM) core, a hydrophobic inner shell which is made of poly-phenylalanine, and a hydrophilic outer shell which is made of poly-lysine or poly-lisine-co-glutamic acid. FIG. 3(b) Represents a synthetic procedure to generate N-caboxyanhydride (NCA) amino acid for the NCA polymerization. FIG. 3(c) Represents a synthetic procedure for constructing a degradable polypeptide nanoparticle. A polypeptide-dendrimer nanoparticle was constructed based on a poly(amidoamine) (PAMAM) polyamine structure. The construction began with a Michael addition and amidation between tri(2-amnoethyl)amine and methyl acrylate. Later a first peptide layer of phenylalanine was polymerized onto the compound 3 backbone through a N-carboxyanhydride polymerization reaction, creating a hydrophobic shell. Next, a second layer of a peptide of lysine was constructed using the same approach, creating a hydrophilic shell. Hydrolysis was conducted to deprotect the lysine side chain amine groups. The polypeptide-dendrimer nanoparticle diameter was characterized with TEM and DLS to be 9.72 nm (in THF) and 12.0 nm (in PBS). FIG. 3(d) Represents a TEM image of the synthesized polypeptide nanoparticle with sub-10 nm diameter. FIG. 3(e) Representative degradation profile of the polypeptide-dendrimer nanoparticle. FIG. 3(f) Represents UV-Vis absorption-based characterization of small molecule (Rhodamine) loading capacity of the polypeptide-dendrimer nanoparticle. FIG. 3(g) Represents single-strand DNA loading capacity characterization through NanoDrop.

FIGS. 4(a)-4(c): Biologically Active Synthetic Nanoparticle Construct Transcribes a Reporter Plasmid and Activates Endogenous Genes. FIG. 4(a) Schematic representation of co-delivering a reporter plasmid and biologically active synthetic nanoparticle construct. After the biologically active synthetic nanoparticle construct and the reporter plasmid localize within the nucleus, transcriptional activity is initiated to produce alkaline phosphatase (ALP), which is secreted by the reporter gene into the culture media. FIG. 4(b) Representation of the ALP fold induction initiated by the biologically active synthetic nanoparticle construct, as compared to controls. FIG. 4(c) Representation of the biologically active synthetic nanoparticle construct's ability to activate target endogenous genes on native DNA.

FIGS. 5(a)-5(d): Controlling Stem Cell Differentiations Using Biologically Active Synthetic Nanoparticle Constructs. Represents the applicability of biologically active synthetic nanoparticle constructs to several different cellular applications. FIG. 5(a) Representation of biologically active synthetic nanoparticle constructs entering cell nuclei. FIG. 5(b) Representation of biologically active synthetic nanoparticle constructs entering cell nuclei, where biologically active synthetic nanoparticle constructs are designed to replicate natural TFs that are specific to myogenic regulatory factors (MRFs), which can induce stem cell myogenesis. FIG. 5(c) Representation of biologically active synthetic nanoparticle constructs entering cell nuclei, where biologically active synthetic nanoparticle constructs are designed to replicate natural TFs that are specific to Sox9, which can induce stem cell chondrogenesis. FIG. 5(d) Representation of biologically active synthetic nanoparticle constructs entering cell nuclei, where biologically active synthetic nanoparticle constructs are designed to replicate natural TFs that are specific to a neural switch gene, which can induce neurogenesis.

FIGS. 7(a)-7(e): Biologically Active Synthetic Nanoparticle Construct as a Degradable Synthetic Transcription Factor. Represents the biologically active synthetic nanoparticle construct performance with adipose-derived mesenchymal stem cells (ADMSCs).

FIG. 7(a) Schematic representation of the biologically active synthetic nanoparticle construct and nuclear co-localization. FIG. 7(b) Representation of fluorescent microscope image (scale bar: 50 µm) for biologically active synthetic nanoparticle construct ADMSCs nuclear uptake, demonstrating that the biologically active synthetic nanoparticle construct could be well-uptaken in ADMSCs within 4 hours after treatment; where FIG. 7(b1) shows the biologically active synthetic nanoparticle construct fluorescence signal, and FIG. 7(b2) shows the biologically active synthetic nanoparticle construct highly localized inside the cellular nucleus. FIG. 7(c) Representation of high magnification fluorescence microscope image (scale bar: 25 µm) for biologically active synthetic nanoparticle construct ADMSCs nuclear uptake, demonstrating that the biologically active synthetic nanoparticle construct was highly localized inside the cellular nucleus structure; where FIG. 7(c1) shows the biologically active synthetic nanoparticle construct fluorescence signal, and FIG. 7(c2) shows the biologically active synthetic nanoparticle construct highly localized inside the cellular nucleus. FIG. 7(d) Representation of biologically active synthetic nanoparticle construct cell viability assay in ADMSCs cell line demonstrating that the degradable biologically active synthetic nanoparticle construct showed excellent bio-compatibility, with 90% cell survival rate, at 100 μg/ml concentration. FIG. 7(e) Representation of time dependent biologically active synthetic nanoparticle construct retention characterization within ADMSCs, demonstrating that nearly 50% of the biologically active synthetic nanoparticle construct could reside inside the nucleus structure for up to 7 days after treatment.

DETAILED DESCRIPTION OF THE INVENTION

1. Overview

Figure 1:
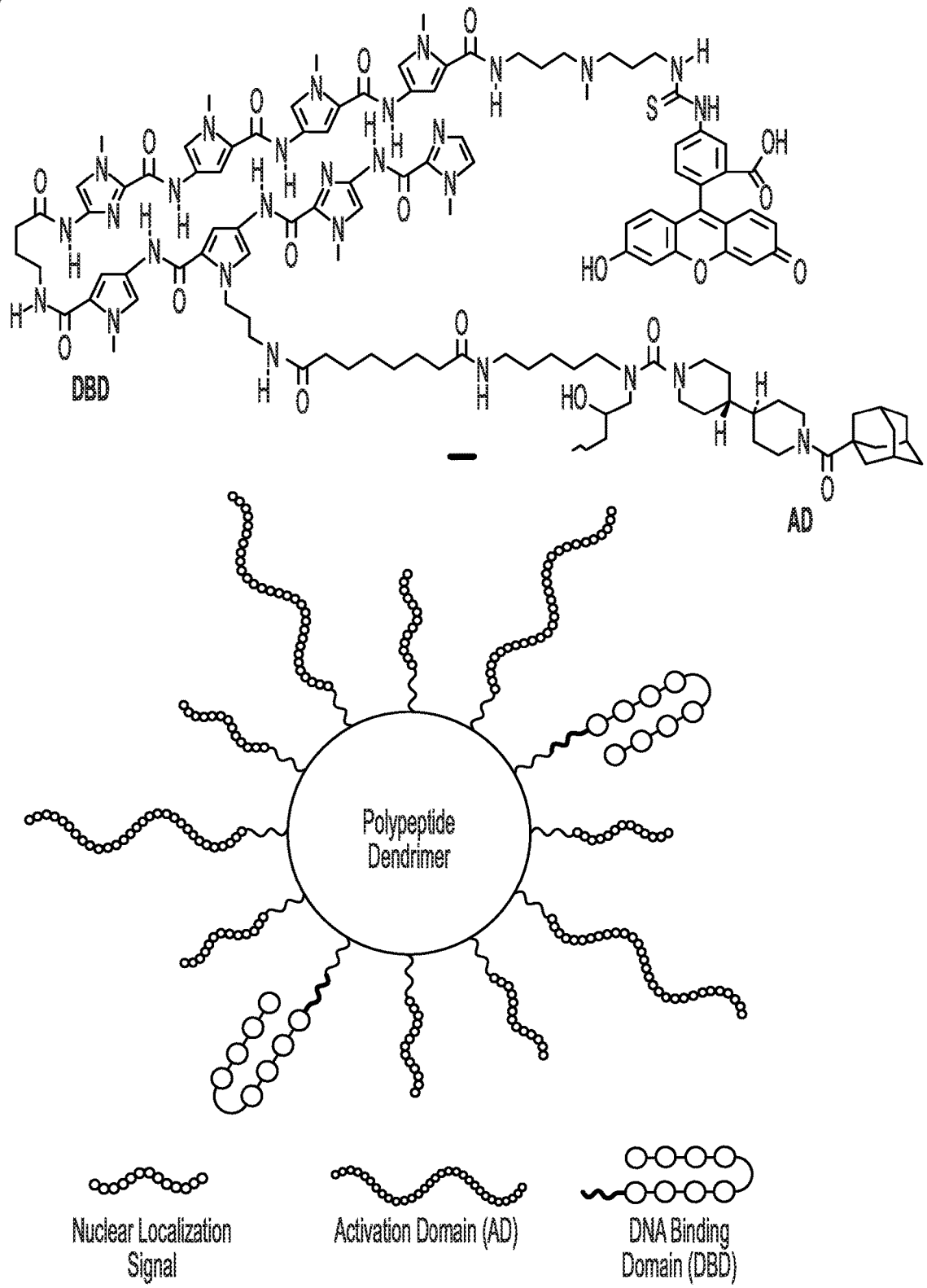
FIG. 1: Schematic Depiction of a Biologically Active Synthetic Nanoparticle Construct. This schematic depiction of an example of a biologically active synthetic nanoparticle construct includes a polypeptide-dendrimer nanoparticle having attached to its surface a plurality of single copies of DBD, a plurality of single copies of NLS, and a plurality of single copies of AD. The presence of the AD, NLS, and DBD allows this example of a biologically active synthetic nanoparticle construct to activate transcription of a target gene.
Figure 2:
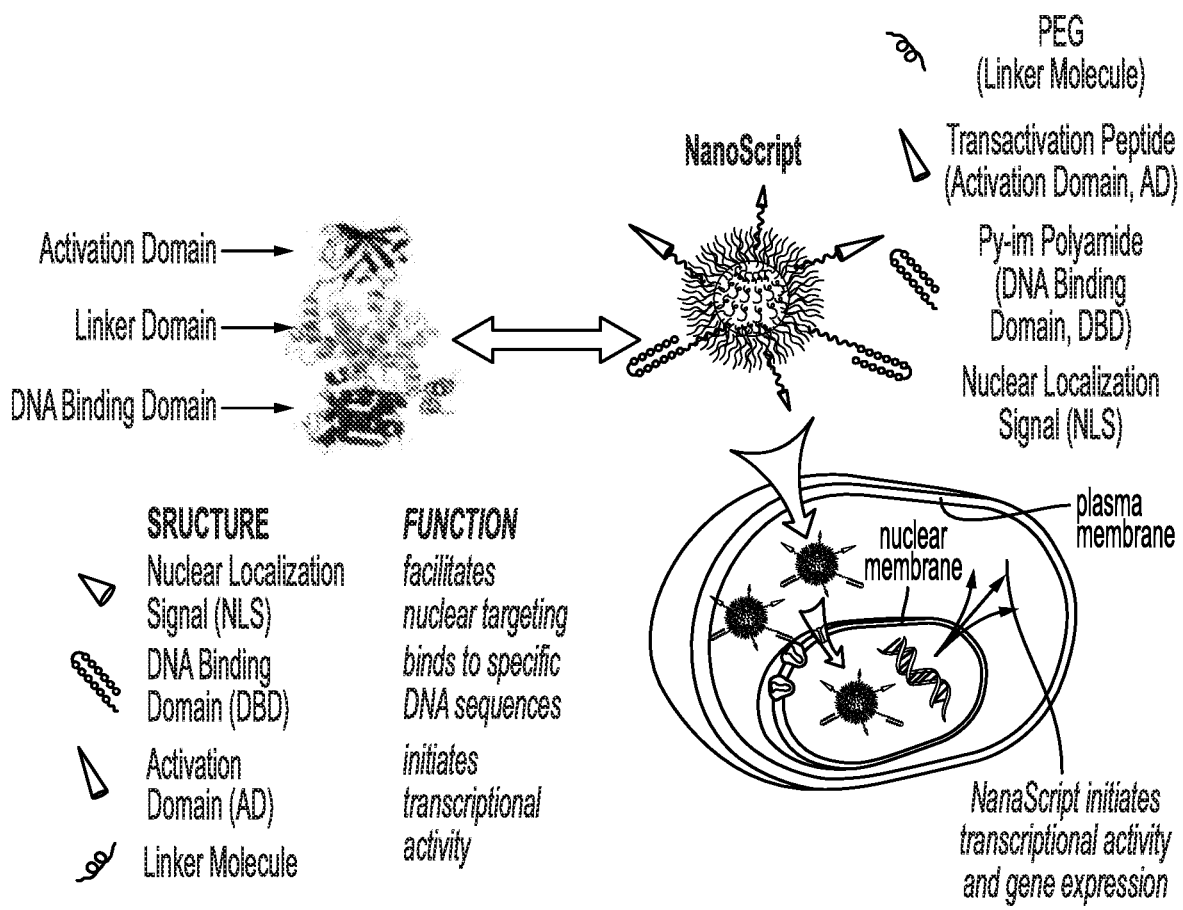
FIG. 2: Schematic Representation and Characterization of Biologically Active Synthetic Nanoparticle Construct Design and Function. Schematic representation of a biologically active synthetic nanoparticle construct designed by assembling the DBD, AD, and NLS, onto a single polypeptide-dendrimer nanoparticle. This platform may replicate the structure and function of natural TFs. This construct penetrates the cell membrane and enters the nucleus through the nuclear receptor with the help of the NLS peptide. Once in the nucleus, the construct interacts with DNA to initiate transcriptional activity and induce gene expression. When comparing the structure of this biologically active synthetic nanoparticle construct to representative TF proteins, the four essential domains are effectively replicated. The polypeptide-dendrimer nanoparticle replicates the linker domain (LD) of a natural TF protein, which fuses the multi-domain protein together.
Figure 3A:
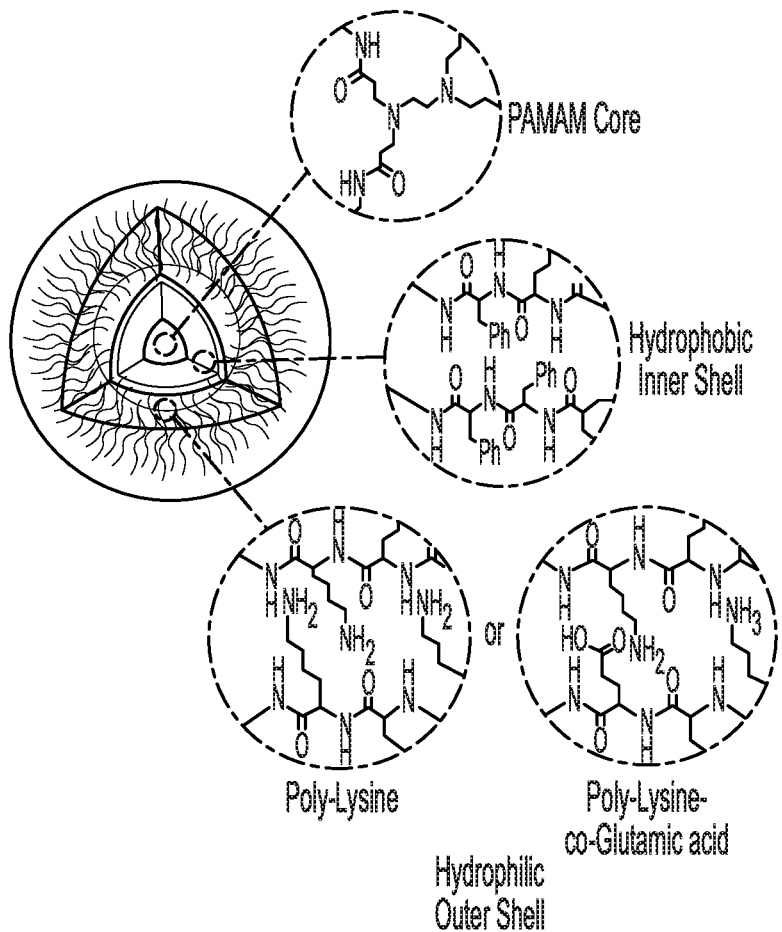
FIGS. 3(a)-3(g): Construction and Characterization of Polypetide-dendrimer Nanoparticle.
Figure 3B:
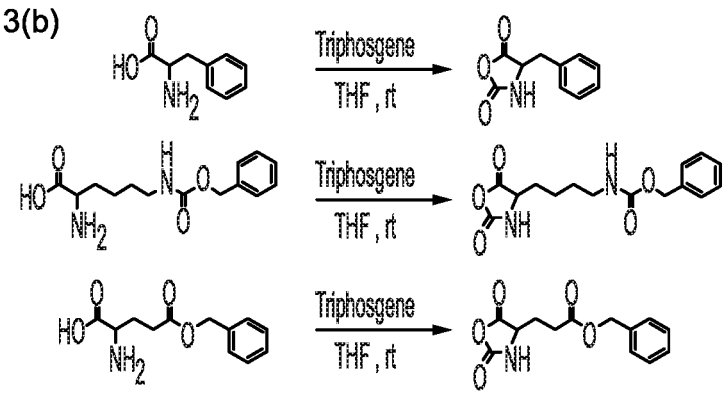
Figure 3C:
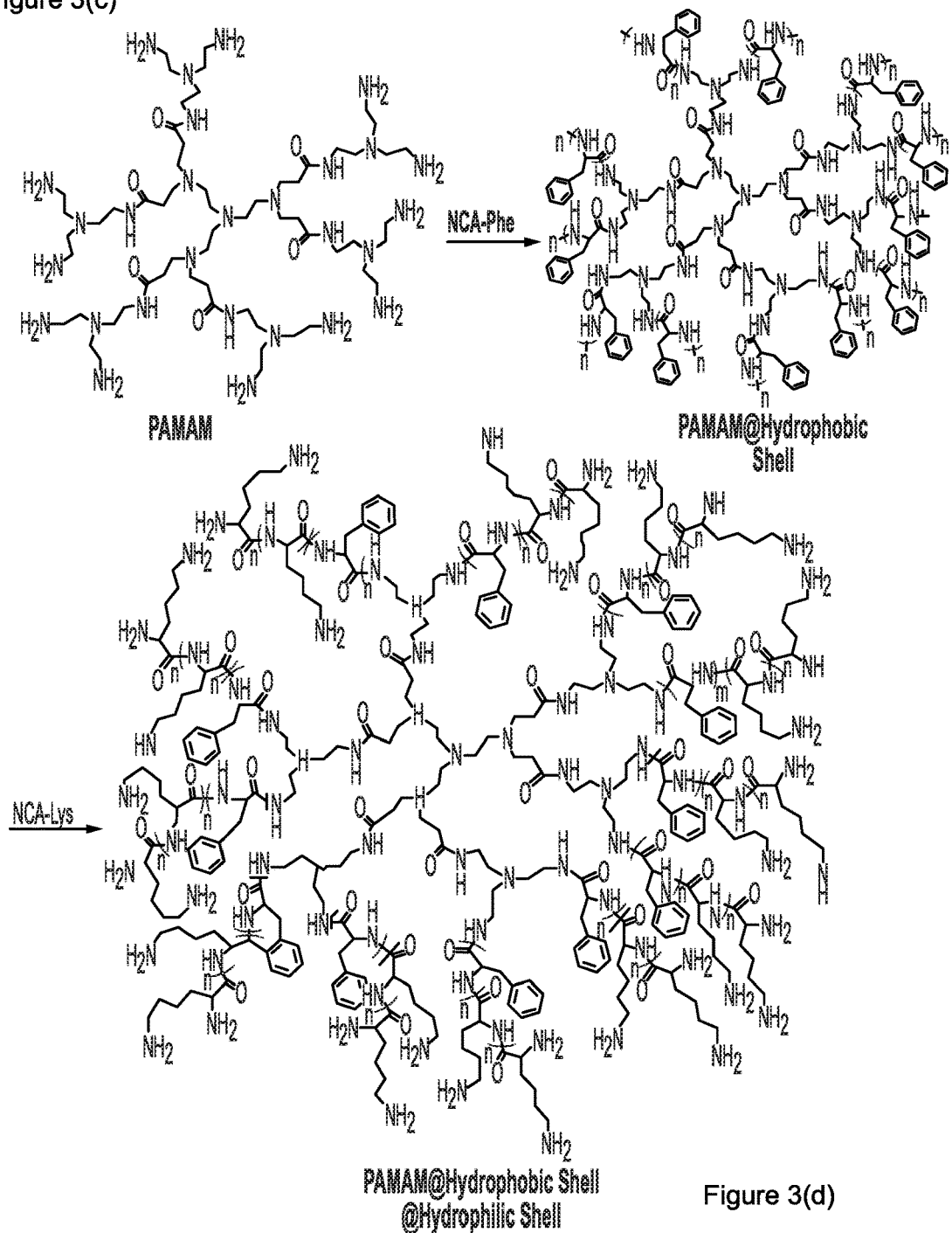
Figure 3D:
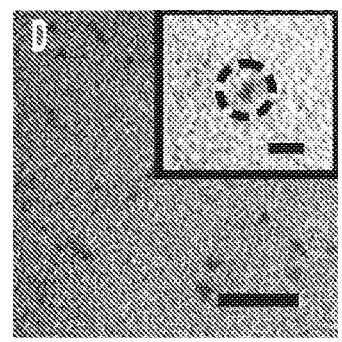
Figure 3E:
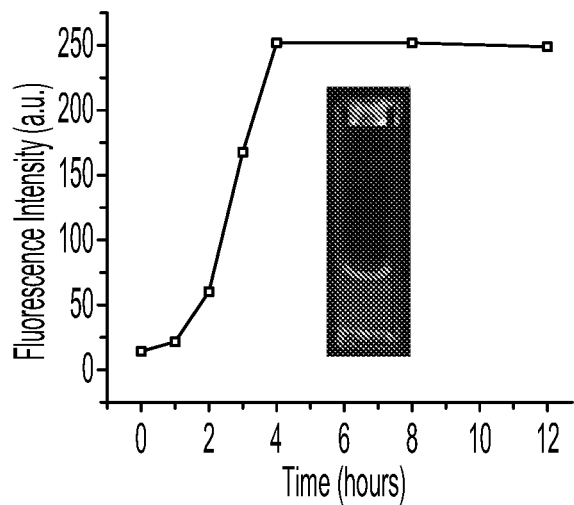
Figure 3F:
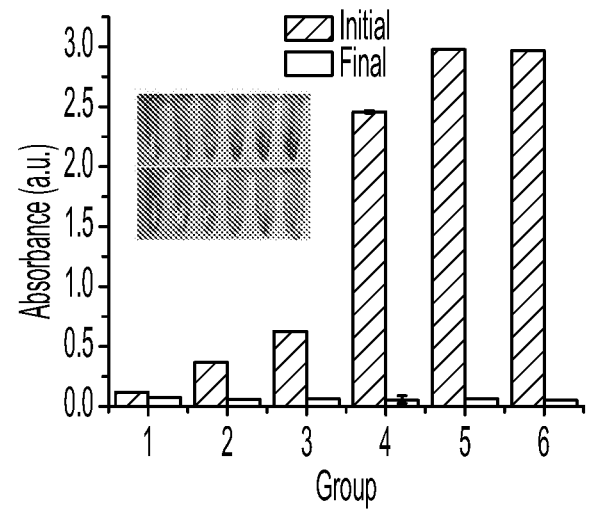
Figure 3G:
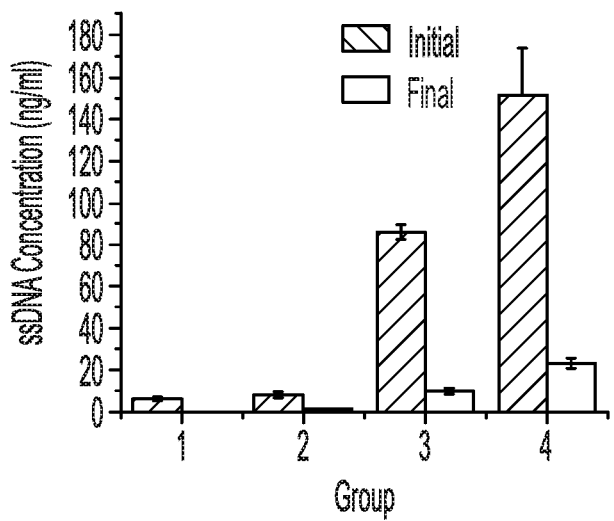
Figure 6:
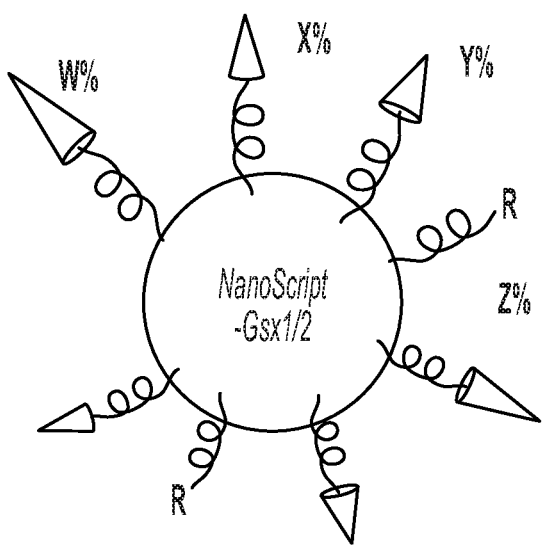
FIG. 6: Advantages of Biologically Active Synthetic Nanoparticle Constructs Over Conventional Viral-vector Methods. Represents the ability to adjust the synthetic transcription factor (STF) ratios on the polypeptide nanoparticle structure, namely the percent of DBD (X %), TD (Y %), NLS (Z %), and other conjugants (W %), to maximize gene expression of a reporter plasmid.
Figure 7A:
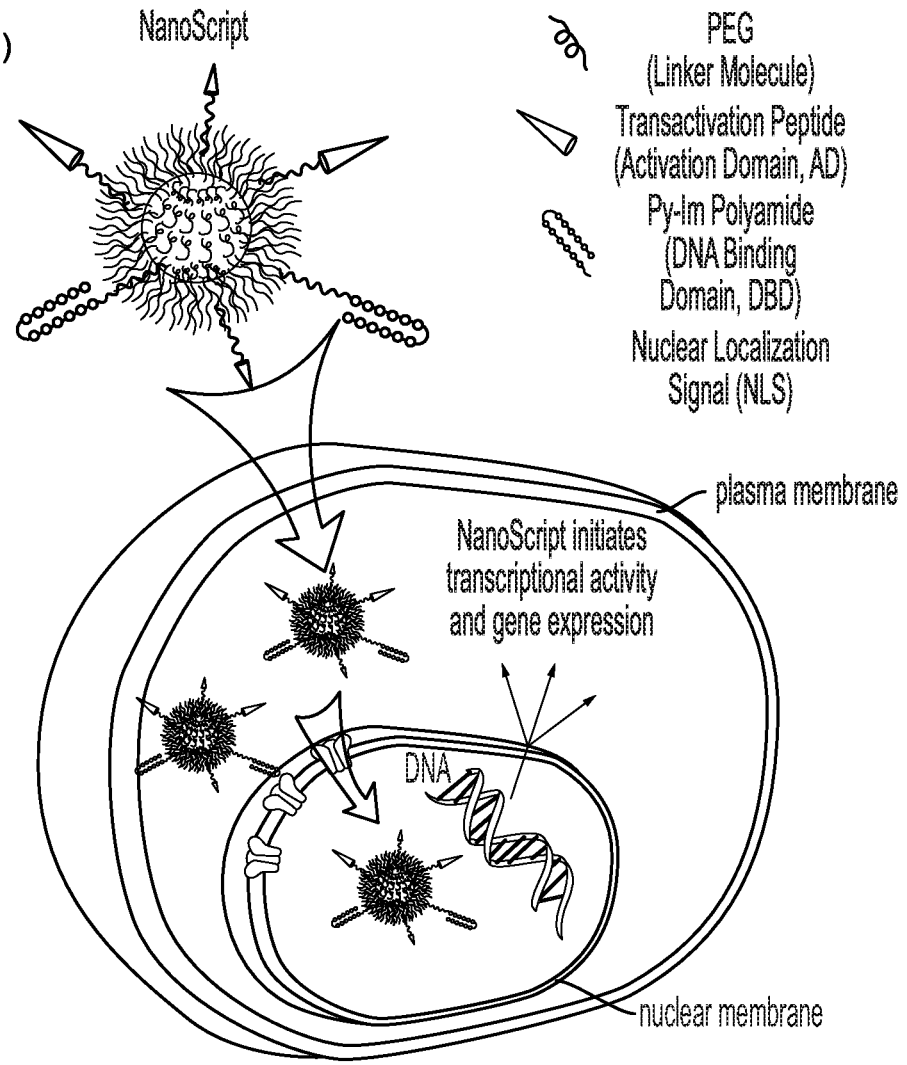

Unless otherwise defined, all technical and scientific terms used herein have the same meaning as commonly understood by one of ordinary skill in the art to which this invention pertains. In the case of conflict, the present document, including definitions, will control.

This invention concerns biologically active synthetic nanoparticle constructs, and their methods of use. The nanoparticle constructs may be used, for example, to enable significant increases in gene expression in, for example, but not limited to, recombinant vectors, as well as expression of endogenous genes in a target organism or tissue sample. Suitable target organisms include any and all organisms of the domain eukaryota. Similarly, the nanoparticle constructs may be used, for example, to enable transcriptional repression in, for example, but not limited to, recombinant vectors, as well as repression of endogenous genes in a target organism or tissue sample. By regulating and/or modifying transcriptional activity, the nanoparticle constructs may be used, for example, to activate or repress stem cell differentiation in a host organism or tissue sample. Furthermore, the nanoparticle constructs may be combined with a delivery vehicle for effective delivery into a host system.

Generally, the biologically active synthetic nanoparticle constructs are polypeptide-dendrimer nanoparticle substrates having attached to their surfaces, a plurality of single copies of DNA binding domains (DBD), a plurality of single copies of nuclear localization signals (NLS), and a plurality of single copies of transcriptional domains (TD).

2. Biologically Active Synthetic Nanoparticle Construct

The present invention provides biologically active synthetic nanoparticle constructs functionalized with DBD, NLS and TD components and optionally other components. The biologically active synthetic nanoparticle constructs are capable of initiating and repressing transcriptional activity and are therefore capable of regulating gene expression in living cells in a non-viral manner.

The biologically active synthetic nanoparticle constructs have a small size, which enables them to permeate the plasma membrane. In one embodiment of the invention, biologically active synthetic nanoparticle constructs have a diameter of no more than 30 nm. Despite their small size, the biologically active synthetic nanoparticle constructs are able to accommodate different types of biomolecules on a single nanoparticle, enabling them to have multifunctional properties. Additionally, the biologically active synthetic nanoparticle constructs are able to initiate strong transcriptional activity of a reporter plasmid, in a dose-dependent manner, in live HeLa cell cultures. The biologically active synthetic nanoparticle constructs can bind to select sequences on native DNA in HeLa cells and initiate transcriptional activity to overexpress endogenous genes. Also, they have enhanced localization within the nucleus, while remaining intact. Under study conditions, the biologically active synthetic nanoparticle constructs were nontoxic to cells. The versatile and tunable properties of the biologically active synthetic nanoparticle constructs establish them as an effective platform for applications that require endogenous gene regulation, such as cellular reprogramming or stem cell differentiation.

The surface of the polypeptide-dendrimer nanoparticle provides a substrate that serves as a base platform upon which the other elements of the biologically active synthetic nanoparticle construct can be bound. The polypeptide-dendrimer nanoparticle has a core-shell morphology, with a core, and inner shell, and an outer shell. The core of the polypeptide-dendrimer nanoparticle is a hydrophobic dendrimer. Suitable dendrimers include those having an amide linker and outer amine functionalization which enable the dendrimer to undergo N-carboxyanhydride polymerization. The dendrimer may be, for example, polyamidoamine (PAMAM), PAMAM with a chiral d-glucose, or a renal cleavable or degradable nanomaterial having multi-amine functionalization, such as for example, an amine-functionalized polyhedral oligosilsesquioxane. Where the dendrimer is PAMAM, each PAMAM skeleton provides 12 primary amine groups for polypeptide formation by N-carboxyanhydride polymerization. The hydrophobic core may be a biodegradable nanomaterial having multi-amine functionalization attached to it.

At least partially surrounding, preferably substantially surrounding, and more preferably completely surrounding the outer surface of the polypeptide-dendrimer nanoparticle core, is an inner shell. The inner shell, which is hydrophobic, enables the polypeptide-dendrimer nanoparticle to maintain a polymer micelle structure, while having an inner hydrophobic reservoir that is able to accommodate small hydrophobic molecules. This advantageously makes it useful, for example, for imaging or therapeutic applications. The hydrophobic inner shell is a polypeptide which may be made, for example, from polymerized hydrophobic amino acids. Suitable amino acids include, for example, glycine, alanine, valine, leucine, isoleucine, phenylalanine, methionine, tryptophan, and cysteine.

At least partially surrounding, preferably substantially surrounding, and more preferably completely surrounding the outer surface of the polypeptide-dendrimer nanoparticle inner shell, is an outer shell. The outer shell, which is hydrophilic, is a polypeptide. It may be made, for example, from polymerized hydrophilic alpha amino acids, which may be selected based on the desired properties. For example, lysine may be selected for the purpose of ligand conjugation or particle charge, glutamic acid or aspartic acid may be selected for surface charge control, and lysine-co-glutamic acid may be selected for all of these properties. In one embodiment, the outer shell polypeptide may have at least one functional group attached to it. Suitable functional groups include, for example, amine, carboxyl, phosphonate, and sulfonate groups. In one embodiment of the invention, the functional group may be a maleimide group, such as for example, sulfosuccinimidyl 4-(N-maleimidomethyl)cyclohexane-1-carboxylate. In one embodiment, the functional group on the outer shell polypeptide may be suitable for bioconjugation, for example via a thiol-maleimide click reaction, between maleimide groups on the polypeptide-dendrimer nanoparticle and thiol functional groups on the DBD, TD and NLS ligands. In another embodiment, the functional group may be selected to provide a particular isoelectric point for the biologically active synthetic nanoparticle construct, which may be desirable to provide the biologically active synthetic nanoparticle construct with an affinity for DNA. In one embodiment of the invention, the outer shell polypeptide may have an isoelectric point of from 6.5 to no more than 8. In another embodiment, the polypeptide polymer may be designed to be poly(Phe)$_m$-b-(Lys)$_n$, where m and n are integers each having a value ranging from 1 to 10 for a positive surface charge; or poly(Phe)$_x$-b-(Lys$_y$/Glu$_z$), wherein x, y and z are integrals each having a value ranging from 1 to 10. The ratio of x and y may be used to modulate the nanoparticle surface charge for different applications (in vitro and in vivo).

In one embodiment of the invention, the diameter of the polypeptide-dendrimer nanoparticle may be tuned by controlling amino acid feeding ratio to the dendrimer core.

In another embodiment of the invention, the polypeptide-dendrimer nanoparticle core may be loaded with at least one of hydrophobic small molecules, such as for example epigenetic modulator or dye; oligonucleotides; ions, such as for example gadolinium, manganese, and rhenium; or a combination thereof, making it useful, for example, for fluorescence and MRT T1 imaging.

The polypeptide-dendrimer nanoparticle outer shell has several moieties attached to it. These moieties are a plurality of single copies of DNA binding domains (DBD), a plurality of single copies of transcriptional domains (TD), a plurality of single copies of nuclear localization signals (NLS), and, and optionally other components. From 10% to 70% (X %) of the moieties on the polypeptide-dendrimer nanoparticle may be DBD; from 10% to 70% (Y %) of the moieties on the polypeptide-dendrimer nanoparticle may be TD; from 10% to 70% (Z %) of the moieties on the polypeptide-dendrimer nanoparticle may be NLS; and optionally from 0% to 40% (W %) of a different component or conjugant. For example, X % may range from about 20% to about 60%, from about 30% to about 50%, or from about 35% to about 45%, etc.; Y % may range from about 20% to about 60%, from about 30% to about 50%, or from about 35% to about 45%, etc.; Z % may range from about 20% to about 60%, from about 30% to about 50%, or from about 35% to about 45%, etc.; and W % may range from about 1% to about 35%, from about 10% to about 30%, or from about 15% to about 25%, etc.

In those embodiments of the invention where the moieties attached to the polypeptide-dendrimer nanoparticle are DBD, TD, and NLS, the sum of the percentage of each moiety, or the sum of X %, Y %, and Z % is no greater than 100%. In those embodiments of the invention where the moieties attached to the polypeptide-dendrimer nanoparticle are DBD, TD, NLS, and at least one other component, the sum of the percentage of each moiety, or the sum of X %, Y %, Z %, and W % is no greater than 100%. In one embodiment of the invention, at least 50% of the ligands on the biologically active synthetic nanoparticle construct are NLS. In another embodiment, at least 60% of the ligands on the biologically active synthetic nanoparticle construct are NLS. Any suitable method can be used to measure the quantity of each moiety (conjugant) attached (conjugated) to the polypeptide-dendrimer. The ratios of each type of moiety attached to the surface of the biologically active nanoparticle construct may be determined by using high-performance liquid chromatography (HPLC) to calculate the concentration differences before and after conjugation of the moieties to the biologically active nanoparticle construct. HPLC analysis is well known in the art and is described, for example, in Patel et al. (ACS Nano. 2014 Sep. 23; 8(9): 8959-67).

The biologically active nanoparticle construct may be tuned, for example by utilizing specific ratios of DBD, TD NLS and other components or conjugants, using specific conjugants, and selecting DBD that target specific genes. For example, the biologically active nanoparticle constructs may be tuned for promoting regeneration during spinal cord injury therapy, by utilizing a biologically active nanoparticle construct having DNA binding domains that target the ASCL1 gene. The ratio of DBD to TD to NLS may be adjusted to provide optimized effects of gene activation or repression. In one embodiment of the invention, the optimization process may begin with the use of a 1:1:1 ratio of DBD:TD:NLS, which may then be systematically adjusted to achieve the desired effects. In one embodiment of the invention, the ratios of NLS and DBD to TD are effective to ensure sufficient nuclear uptake, as observed by confocal imaging and/or measured using polymerase chain reaction (PCR); and provide a binding affinity essentially equivalent to naturally-occurring DNA binding proteins. By "a binding affinity essentially equivalent to naturally-occurring DNA binding proteins," is meant that the DNA binding domains of the invention have a binding affinity that is functionally comparable to the binding affinity of natural transcription factors, such that the biologically active nanoparticle construct binds to the DBD with an affinity having an equilibrium dissociation constant ($K_d$) of about 1 mM or less.

The single copies of DNA binding domains (DBD) are moieties which are capable of binding directly to target nucleotide sequences of interest, for example but not limited to, a specific DNA sequence in a promoter region. This invention utilizes DBD for purposes of binding to nucleotide targets of interest to modulate transcription, for example, either activating or repressing transcription, and thus affecting certain biological processes, such as stem cell differentiation and cellular programming applications. The DNA binding domain is preferably a hairpin polyamide sequence motif including N-methylpyrrole (Py) and N-methylimidazole (Im), as hairpin polyamide sequences exhibit high tunability and binding specificity, as well as small molecular size. Hairpin polyamides function by binding to the minor groove of DNA, through hydrogen bond interactions, with a binding affinity comparable to naturally occurring DNA-binding proteins, as the Py and Im amino acids complement the A-T and G-C motifs on the DNA respectively. However, other DNA binding domains are embodied by the present invention, and may include, for example but not limited to, zinc finger domains, triplex-forming oligonucleotides (TFOs), transcription activator-like effectors, oligonucleotide analogs, locked-nucleic acids, and peptide nucleic acids.

In some embodiments, TFOs are used as the DBD for specific and efficient targeting of genes. Construction and use of TFOs are well known in the art (see, e.g., Dev P. Arya Chem Res 44(2):134-146, 2011). Advantages of using TFOs include their long binding sequence and specificity for the target gene. For example, TFOs are major groove binding ligands that can target specific DNA sequences by forming DNA triple helixes via Hoogsteen hydrogen bonding interactions between the TFOs and the targeted oligo-purine strand of the duplex DNA. Triplex-formation occurs in two motifs, distinguished by the orientation of the third strand on the purine-rich strand of the target duplex. The triple-helix target sites (TTS) are over-represented in the human genome and especially at promoter regions. Examples of TFOs that can be used include the following:

```
Gfi1:
                                            (SEQ ID NO: 1)
5' GAGGAAAAAAAGGA 3'

(SEQ ID NO: 2)
5' TTTTTCTTTCCTTCT 3'

(SEQ ID NO: 3)
5' TTCTTTTTTCCTTTT 3'

(SEQ ID NO: 4)
5' TTTCTCTTTTCTTTTTCTTTTT 3'

(SEQ ID NO: 5)
5' GAGAAAAAGGGAAGGA 3'

(SEQ ID NO: 6)
5' AGAGGTGAAAAAAAAAAA 3'

(SEQ ID NO: 7)
5' TCTTCCTTCTCCTTC 3'

(SEQ ID NO: 8)
5' AAGGGGAGAAGAATGGAAAGAGGA 3'

(SEQ ID NO: 9)
5' AAAAAAGGGGACAAGA 3'

Pou4f3:
                                            (SEQ ID NO: 10)
5' TCTCTTTCCCTCTCCTTCC 3'

(SEQ ID NO: 11)
5' CCCCCCCCCCCTCCC 3'

(SEQ ID NO: 12)
5' AGAAAAGGGAGAAAAGAAGAGG 3'

(SEQ ID NO: 13)
5' TCTCGTCTTTTTCTCTT 3'

(SEQ ID NO: 14)
5' AAGGGGAAAAGGGAAA 3'

(SEQ ID NO: 15)
5' GAAAAGAAGAATGGGA 3'

(SEQ ID NO: 16)
5' TTCCCTCTCCTTTCTTCTCCCTTC 3'

(SEQ ID NO: 17)
5' TCTCTCTTTTTCTCC 3'

(SEQ ID NO: 18)
5' CCCCCTCTCCCCTCC 3'

(SEQ ID NO: 19)
5' CTCTCCCCCTCCCCTC 3'

Atoh1:
                                            (SEQ ID NO: 20)
5' CCCCCTCTTTCTTCTCTTCTTTTTCCCTCCCTCCCTCCTC
TTCTT 3'

(SEQ ID NO: 21)
5' GGAAAAGAAAAGAAA 3'

(SEQ ID NO: 22)
5' AAAAGGGGGAAATAAGG 3'

(SEQ ID NO: 23)
5' TTTTCTTCCTTTTTTTTTTTTTT 3'

(SEQ ID NO: 24)
5' CTCCTCCCTTTTTTTT 3'
```

Nuclear localization signals (NLS) are amino acid sequences that allow for the passage or import of a substance, typically an endogenous protein, into the cell nucleus, by nuclear transport. This invention utilizes single copies of NLS to allow for effective nuclear transport of the biologically active synthetic nanoparticle construct into the nucleus, so as to modulate transcriptional activity, as in eukaryotes, transcription occurs endogenously in the nucleus. Classical NLSs are typically classified as monopartite or bipartite. Non-classical NLSs include those derived from the M9 domain of hnRNP A1 and the KIPIK (SEQ ID NO: 25) sequence in yeast transcription repressor Mata2, and like classic NLS, are embodied by the present invention. Preferred NLS domains include those derived from SV-40 antigens, for example, domains bearing the sequence PKKKRKV (SEQ ID NO: 26). Others include those derived from HIV-1. One of ordinary skill in the art will recognize that any monopartite NLS following the Chelsky sequence K-K/R-X-K/R (SEQ ID NO: 27) is embodied by the present invention. Other NLS domains are embodied by the present invention, and include, for example but not limited to, bipartite NLSs such as those derived from nucleoplasmin, and other NLSs such as those listed in the table below:

| Name | Sequence |
| --- | --- |
| TAT (SEQ ID NO: 28) | GRKKRRQRRRPPQ |
| Penetratin (SEQ ID NO: 29) | RQIKIWFQNRRMKWKK |
| MAP (SEQ ID NO: 30) | KLALKLALKALKAALKLA |
| Transportin/TP10 (SEQ ID NO: 31)/ (SEQ ID NO: 32) | GWTLNS/ AGYLLGKINLKALAALAKKIL |
| VP22 (SEQ ID NO: 33) | NAKTRRHERRRKLAIER |
| MPG (SEQ ID NO: 34) | GALFLGFLGAAGSTMGA |
| Pep1 (SEQ ID NO: 35) | KETWWETWWTEWSQPKKKRKV |
| pVEC (SEQ ID NO: 36) | LLIILRRRIRKQAHAHSK |
| YTA2 (SEQ ID NO: 37) | YTAIAWVKAFIRKLRK |
| YTA4 (SEQ ID NO: 38) | IAWVKAFIRKLRKGPLG |
| M918 (SEQ ID NO: 39) | MVTVLFRRLRIRRACGPPRVRV |
| CADY (SEQ ID NO: 40) | GLWRALWRLLRSLWRLLWRA |

The transcriptional domains of the invention may be single copies of activation domains (AD) or single copies of repression domains (RD). Activation domains (AD) are those domains that are capable of activating transcriptional activity, for example, by recruiting proteins such as RNAP, and other factors that are required for transcriptional activation. ADs may be involved in triggering signaling cascades, leading to the expression of desired genes. In the present invention, ADs are preferably, but not necessarily, peptide sequences, and the peptide sequences are preferably, but not necessarily, synthesized in the D-isomer, in order to resist intracellular degradation. One explicitly non-limiting example of an AD peptide domain is SGLMDLDFD-DLADSGLMDLDFDDLADSGC (SEQ ID NO: 41). Other ADs are embodied by the present invention and may include, for example but not limited to, peptoids, amphipathic isoxasolidine, wrenchnolol, and amphipathic helix peptides.

Repression domains (RD) are those domains that are capable of repressing transcriptional activity, for example, by activating repressor proteins. In the present invention, RDs are preferably, but not necessarily, peptide sequences, and the peptide sequences are preferably, but not necessarily, synthesized in the D-isomer, in order to resist intracellular degradation. A list of RDs that are embodied by the present invention include, but are not limited to, those found in the table below:

| Repression Domains |
| --- |
| WRPW (SEQ ID NO: 42) |
| RLITLADHICQIITQDFAR (SEQ ID NO: 43) |
| QINDLYSTDRPESAEAPDLQSWELR (SEQ ID NO: 44) |
| ELQKSIGHKPEPTEEWELIKTVTEAHV (SEQ ID NO: 45) |
| STPSSKTKDLGHNDKKSS (SEQ ID NO: 46) |

The biologically active synthetic nanoparticle constructs may comprise further domains (conjugants) beyond the DBD, NLS, and TD, which may be biologically active or inert. They may serve a purpose, for example, but not limited to, increasing nuclear permeability, facilitating stability of the nanoparticle construct, increasing the safety of the nanoparticle construct, decreasing toxicity, or interacting with various cellular components. These additional domains may participate in transcriptional activation or repression, in a manner consistent with, or independent of, any AD or RD. They may synergistically increase the efficiency or potency of the biologically active synthetic nanoparticle construct. These examples are not meant to be limiting, but merely demonstrative of the possibilities of additional domains.

The various domains of the biologically active synthetic nanoparticle construct, including the DBD, NLS, TD, or any other domains, are bound to the surface of the polypeptide-dendrimer nanoparticle. Preferably, the domains are bound covalently via a crosslinker, for example, a crosslinker having a formula SH—R—COOH. The R group may be, for example, but not limited to, any derivative of an alkyl or alkoxy chain, straight chain, branched, or otherwise, so long as the chain is not too short, for example having a backbone that is less than 3 carbons in length, or too long, for example having a backbone that has greater than 200 carbons. For example, the R group may be polyethylene glycol (PEG) or undecanoic acid. One of ordinary skill in the art will recognize that there are many crosslinkers that are suitable for the purposes of this invention. Too short a chain risks aggregation, and too long a chain risks the overall size of the biologically active synthetic nanoparticle construct being too large to enter the nucleus, thus rendering the construct ineffective. Preferably, the domain amino groups are coupled to crosslinker carboxylic acids via conventional EDC/NHS coupling, however one of ordinary skill in the art will recognize that there are many other chemical routes to conjugate the molecules, for example but not limited to, active ester coupling utilizing carbodiimides, such as those reactions utilizing dicyclohexylcarbodiimide (DCC) and diisoproylcarbodiimide (DIC); or coupling reactions utilizing triazoles, such as 1-hydroxy-benzotriazole (HOBt) and 1-hydroxy-7-aza-benzotriazole (HOAt).

The multifunctionality of the biologically active synthetic nanoparticle construct provides the nanoparticle construct with different types of functionality. In one embodiment of the invention, the nanoparticle may be designed to have at least one of the following physiochemical properties: biodegradable (for example, through enzymatic amide dissociation), biocompatible, stable in physiological conditions, or possessing small molecule or ion loading capacity enabling non-invasive imaging.

3. Methods of Use of Biologically Active Synthetic Nanoparticle Constructs

A. Transcriptional Activation

Endogenous genes are transcribed when transcriptional basal machinery, which includes compounds, such as for example, general transcription factors (TFs), RNAP, SAGA, and mediators, are directed to a particular target gene sequence, and thus initiate transcription. In some embodiments of the invention, the biologically active synthetic nanoparticle constructs of the invention are useful for, among other things, transcriptional activation of particular target genes or other DNA sequences. As noted hereinabove, the biologically active synthetic nanoparticle construct of the invention has a polypeptide-dendrimer nanoparticle, to which is attached DBD, NLS, and TD. In those embodiments of the invention where transcriptional activation is sought, the transcriptional domains (TD) are activation domains (AD). The biologically active synthetic nanoparticle constructs mimic natural transcription factors, which have DBD and AD. The NLS allow the biologically active synthetic nanoparticle constructs to enter the nucleus, which is essential because transcription takes place in the nucleus. In the nucleus, the AD are involved in recruitment of the endogenous transcriptional basal machinery, such as RNAP and mediators, thus initiating transcription. The DBD binds to enhancer regions of DNA, allowing the AD to recruit the components needed for transcriptional activation.

B. Transcriptional Repression

In some embodiments of the invention, the biologically active synthetic nanoparticle constructs of the invention are useful for, among other things, transcriptional repression of particular target genes or other DNA sequences. As noted herein-above, the biologically active synthetic nanoparticle construct of the invention has a polypeptide-dendrimer nanoparticle, to which is attached DBD, NLS, and TD. In those embodiments of the invention where transcriptional repression is sought, the transcriptional domains (TD) are repression domains (RD). The RD may enhance the efficacy of transcriptional repression by activating repressor proteins, which then in turn bind to silencer regions. As with transcriptional activation, the NLS allows the biologically synthetic nanoparticle constructs to enter the nucleus, which is essential because transcription takes place in the nucleus. However, unlike with transcriptional activation, here, the DBD has a different role. Rather than the DBD binding at an enhancer region and recruiting transcriptional machinery proteins, as is the case with transcriptional activation, in transcriptional repression, the DBD may bind at or near the promoter region and physically block RNAP from initiating transcription, via steric hindrance.

C. Modulation of Stem Cell Differentiation

In some embodiments of the invention, the biologically active synthetic nanoparticle constructs are useful for modulating stem cell differentiation. The ability of the biologically active synthetic nanoparticle constructs of this invention to either activate, or repress transcription in a non-viral manner, makes them useful for stem cell differentiation applications. In preferred embodiments, the stem cells undergoing differentiation are adipose-derived mesenchymal stem cells (ADSCs). ADSC, including adipose-derived mesenchymal stem cells (ADMSCs), are multipotent stem cells that have been shown to differentiate into osteogenic, chondrogenic, adipogenic, myogenic, or neurogenic lineages.

D. Vehicle Delivery Platform

In some embodiments of the invention, the biologically active synthetic nanoparticle constructs may be used as medical devices. In this embodiment, the biologically active synthetic nanoparticle constructs can be polypeptide-dendrimer nanoparticles having attached to their surfaces any combination of DBD, NLS and either AD or RD, as disclosed in this invention. In these embodiments, at least one transcription pre-initiation complex (TPC) ligand is attached to the surface of the polypeptide-dendrimer nanoparticle, the TPC being designed to direct the biologically active synthetic nanoparticle construct to a specific area of an organism. The TPC is made up of various proteins, including RNAP, mediators, and other proteins and/or enzymes, that work synergistically to initiate transcriptional activity. Where the TD used are AD, the AD may function to recruit the TPC to binding sites on targeted genes, and may initiate transcriptional activity of those targeted genes.

A transport vehicle for implementation of the biologically active synthetic nanoparticle constructs may come in a variety of forms, based upon the particular tissue which is affected by the cell differentiation medical device. The inclusion of the TPC in the biologically active synthetic nanoparticle construct ensures that the cell differentiation medical device is directed to where it is needed within the organism.

The transport vehicle may optionally include components for regeneration of tissues. ADSCs may be included with the cell differentiation medical device in the transport vehicle. For internal tissue use, the transport vehicle may optionally be an intravenous drip including a saline solution and the cell differentiation medical device. The intravenous needle used and any container used should be sized so as to ensure the free flow of the intravenous drip into the body.

For topical use, the transport vehicle may optionally include a biodegradable polymer scaffold.

The transport vehicle may be a biodegradable hydrogel, which is useful for direct topical application of the cell differentiation medical device to a specific area of a surface of an organism. A hydrogel may significantly enhance the use of a growth media, for cellular growth upon stimulation by the biologically active synthetic nanoparticle constructs of the cell differentiation medical device.

E. Tissue Regeneration Some embodiments of the invention include methods to regenerate tissue. The method may involve the steps of preparing any cell differentiation medical device, as disclosed herein, and delivering the cell differentiation medical device to an organism, by means that ensure that the cell differentiation medical device is directed to an area, or areas, where tissue regeneration is desired. The method may also include the steps of combining a cell type (somatic cell or stem cell) that can be induced to generate functional cells for the tissue regeneration and transplantation, saline solution, and the cell differentiation medical device, in an intravenous solution, and delivering the intravenous solution to tissue. The method may also further include the step of preparing any cell differentiation medical device, as disclosed herein, and attaching the device topically to an organism.

4. Method of Making Biologically Active Synthetic Nanoparticle Constructs

The biologically active synthetic nanoparticle construct of the invention may be made by first creating a hydrophobic dendrimer core, by performing a Michael addition and amidation reaction between an amine and an acrylate, creating a dendrimer having an amide linker and outer amine functionality suitable for initiating N-carboxyanhydride (NCA) polymerization. Any suitable amine may be used, such as, for example tri(2-aminoethyl)amine, ethylene diamine, diaminobutane, diaminohexane, diaminodecane, or a combination thereof. Any suitable acrylate may be used, and in one embodiment of the invention, the acrylate is methyl acrylate.

Subsequently, a hydrophobic inner shell is formed on top of the surface of the dendrimer core, by polymerizing hydrophobic amino acids, by N-carboxyanhydride (NCA) polymerization, in the presence of the nanoparticle core, to form a polypeptide shell that at least partially covers the outer surface of the dendrimer core. Preferably the inner shell substantially covers the surface of the hydrophobic dendrimer core. More preferably the inner shell completely covers the surface of the nanoparticle core. Suitable hydrophobic amino acids include, for example, glycine, alanine, valine, leucine, isoleucine, phenylalanine, methionine, tryptophan, and cysteine. By "N-carboxy-anhydride polymerization," herein is meant ring-opening polymerization of α-amino acid N-carboxyanhydride (NCA) monomers, which is well known in the art (See e.g. H. R. *Kricheldorf, in Models of Biopolymers by Ring-Opening Polymerization*, Penczek, S. Ed., CRC Press, Boca Raton, (1990). In general terms, NCA polymerizations can be classified into two categories based on the type of initiator used: either a nucleophile (typically a primary amine) or strong base (typically a sodium alkoxide). In the present invention, the NCA polymerization utilizes an amine initiator, and is used to graft polypeptide chains to various amine functionalized nanostructures.

Next, a hydrophilic outer shell is formed on top of the surface of the hydrophobic inner shell, by polymerizing hydrophilic alpha amino acids, by N-carboxyanhydride polymerization, in the presence of the previously formed core-shell structure, to form a polypeptide outer shell that at least partially covers the outer surface of the core-shell structure. Any suitable alpha amino acid may be used, such as for example, lysine, arginine, histidine, aspartic acid and glutamic acid.

The DBD, TD, and NLS are then conjugated onto the outer surface of the hydrophilic outer shell by covalent bonding, preferably utilizing a crosslinker, as described herein-above.

The size of the biologically active synthetic nanoparticle construct may be tuned by controlling the NCA amino acid feeding ratio to the hydrophobic dendrimer core. Since the number of primary amines per dendrimer molecule is known, by tuning the NCA amino acid and dendrimer core molar ratio in the polymerization precursor solution, the amino acid moieties polymerized on each primary amine can be changed, resulting in tuning of the overall size of the nanoparticle.

EXAMPLES

A. Synthesis of Biologically Active Synthetic Nanoparticle Constructs Example A1

Synthesis of Polypeptide-Dendrimer Nanoparticle:
A synthetic peptide nanoparticle was constructed based on a poly(amidoamine) (PAMAM) polyamine structure. The synthesis began with a Michael addition and amidation between tri(2-aminoethyl)amine and methyl acrylate. Later, a first peptide layer of phenylalanine was polymerized onto the compound 3 backbone through a N-carboxyanhydride (NCA) polymerization reaction. A second layer of peptide of lysine was constructed through the same approach. Hydrolysis was conducted to deprotect the lysine side chain amine groups. The peptide nanoparticle diameter was characterized by TEM and DLS to be 9.72 nm (in THF) and 12.0 nm (in PBS). Dye conjugation was achieved using a reaction between FITC-isocyanate and the surface primary amine. Due to the highly positive charge displayed by the peptide nanoparticle, which was +33.9 my (zeta potential), the surface was coated with 2000 kDa polyethylene glycol (PEG) for the mediation of the surface charge. To achieve the optimal size dependency for uptake, different nanoparticle sizes (5, 10, 20 and 30 nm) were checked for uptake efficiency. Additionally, the size and metal ion doping composition of the dendrimer core was optimized to achieve the highest MRI contrast. The peptide nanoparticles were characterized by dynamic light scattering (DLS) and transmission electron microscope (TEM) for size and monodispersity. Additionally, inductively coupled plasma optical emission spectroscopy (ICP-OES) and scanning transmission electron microscopy—electron loss spectroscopy (STEM-EELS) was used to check for the compositions and structure of the dendrimer core, hydrophobic shell and hydrophilic shell.

Example A2

Synthesis of Biologically Active Synthetic Nanoparticle Construct:
Polypeptide-dendrimer nanoparticles were prepared as described in example A1, above. Hairpin polyamides were generated using a well-known solid-state synthesis procedure, to act as the DNA binding domain having pyrrole (Py) and imidazole (Im) groups. A plurality of a well-established transactivation peptide (LMDLDFDDLADS (SEQ ID NO: 47)) known to have a superior efficacy of recruiting the transcription pre-initiation complex (TPC) and inducing gene expression in-vitro, was used as the AD. The TPC contained RNA polymerase II, general transcription factors, mediators and other cofactors to regulate transcriptional activity. Since transcription occurs in the nucleus, efficient nuclear uptake of the biologically active synthetic nanoparticle construct was essential. To facilitate cell penetration and nuclear localization of the biologically active synthetic nanoparticle construct, a previously designed membrane peptide, TAT (CALNNAGRKKRRQRRR (SEQ ID NO: 48)) was used as the NLS. The polypeptide-dendrimer nanoparticle was functionalized with thiol-PEG molecules commonly used to increase solubility, enhance stability in various physiological conditions, prevent non-specific interactions, and to act as a spacer. After the polypeptide-dendrimer nanoparticles had been functionalized with the PEG-terminated hairpin polyamides targeting the aforementioned sequences, a biologically active synthetic nanoparticle construct—ASCL1 complex was formed with the attachment of membrane-penetrating peptide. Well-established EDC/NHS coupling chemistry was used to conjugate the amine-terminated synthetic transcription factors onto PEG, and then onto the polypeptide-dendrimer nanoparticles, through a thiol-ene click reaction, in specific ratios. The ratio of AD:DBD:NLS played a critical role in dictating transcriptional activity, because natural transcription factors contain varied ratios of these domains. A library of biologically active synthetic nanoparticle construct—ASCL1 complexes were synthesized using different ratios of synthetic transcription factors. UV/Vis absorption spectroscopy was used to confirm surface functionalization. DLS and TEM were used to confirm monodispersity of particles. Nuclear magnetic resonance (NMR) spectroscopy and high pressure liquid chromatography (HPLC) were used to confirm the final ratio of the individual components of the polypeptide-dendrimer nanoparticles.

B. Investigation of Performance of Biologically Active Synthetic Nanoparticle Constructs Example B1

Investigation of Cellular Uptake, Nuclear Localization and Transcriptional Activity of Biologically Active Synthetic Nanoparticle Construct Complexed with ASCL1:
Biologically active synthetic nanoparticle constructs complexed with ASCL1 were prepared as described in example A, above. Two critical factors needed to be optimized before performing any axon regeneration studies: i) high nuclear localization of the nanoparticle constructs, and (ii) maximal gene expression of targeted transcription factors using the biologically active synthetic nanoparticle constructs. To this end, first, the nanoparticle constructs (1 nm-100 nM) were delivered to adult neurons, and then the cell viability was evaluated using MTS assays. To evaluate cell or nuclear uptake, dye-labeled nanoparticle constructs were delivered to neurons and uptake efficiency was monitored using fluorescence or confocal microscopy to visualize the nanoparticle construct localization. Additionally, nuclear localization of the nanoparticle constructs was performed using transmission electron microscopy (TEM) of cellular cross sections, and three-dimensional structured illumination microscopy (3D-SIM), which is a super-resolution microscope capable of visualizing interactions between chromatin and nanoparticle constructs. After testing several STF ratios, the optimal conditions for nanoparticle constructs for maximum nuclear localization were identified. The ratio of AD:DBD:TAT/NLS was adjusted to determine, for example whether a high ratio of NLS/TAT is required for nuclear translocation of nanoparticle constructs (which is one of the most critical barriers for effective gene activation); or whether a minimal ratio of hairpin polyamide DBD is required because of its high binding affinity to DNA; and whether the ratio of DBD should be higher than AD to mimic potent endogenous TFs. Quantitative polymerase chain reaction (qPCR) was then performed to determine transcript levels of target genes, specifically ASCL1, after transfection with the nanoparticle constructs to determine its transcriptional activity.

The results demonstrated (i) the successful synthesis of all of the components of a synthetic transcription factor for the activation of the endogenous gene to conjugate on polypeptide based nanoparticles to generate biologically active synthetic nanoparticle constructs complexed with ASCL; and (ii) the delivery of the biologically active synthetic nanoparticle constructs complexed with ASCL1 promoted neuronal differentiation through the mimic of ASCL1 function in iPSC neuronal differentiation.

Example B2

Investigation of Biologically Active Synthetic Nanoparticle Construct Induced Neurogenesis in iPSCs, Astrocytes and Fibroblasts and Transplantation into Spinal Cord Injury Model:

As the first step toward treatment and potential translation into the clinic, the biologically active synthetic nanoparticle construct in vitro delivery into cells, and subsequent transplantation into mouse spinal cord injury (SCI) models, was tested. Induced pluripotent stem cells (iPSCs) were chosen, as they represent a model cell line for transplantation, since they are patient specific, and overcome several limitations of cell transplantation therapies such as immune rejection. Astrocytes and fibroblasts were chosen as they make up a large part of the scar that is formed after spinal cord injury, and therefore are an ideal candidate for transdifferentiation into neurons. To attain these objectives, tests were performed to determine whether transplantation of nanoparticle-construct-derived functional neurons in the mouse SCI model would show rehabilitation of spinal cord functions.

Rats from the Young lab, which has established a standardized rat lumbosacral spinal cord injury (SCI) model that causes consistent motoneuronal loss and behavior deficits, were studied. Contusion of the rat spinal cord at the T13-L1 vertebral junction, with a 10 gram weight dropped 25 or 50 mm, resulted in graded lumbosacral SCI, accompanied by reproducible graded tibial and peroneal motoneuronal losses, white matter losses, peripheral nerve axonal diameter decrease, reduced myelinated axonal thickness, and atrophy of the tibialis anterior (TA) and gastrocnemius (GA) muscles, as well as easily quantifiable measurement in both the static and walking footprints of the rats. This model shows reproducible anatomical, histological and functional outcomes that are similar to human lumbosacral injures and can be used to assess regenerative therapies of lumbosacral SCI.

Example B2.1

Investigation of the Effects of Biologically Active Synthetic Nanoparticle Construct-ASCL1 Complexes on Promoting Neuro Genesis In Vitro in IPCSs, Astrocytes and Fibroblasts In vitro analyses were performed to determine the effects of biologically active synthetic nanoparticle construct-ASCL1 (Achaete-Scute Family BHLH Transcription Factor 1) complexes on promoting neurogenesis in various cell lines. IPSCs, astrocytes, and fibroblasts were transfected with biologically active synthetic nanoparticle construct-ASCL1 at optimum conditions determined from Example A. biologically active synthetic nanoparticle constructs with concentrations ranging from 1-100 nM were treated to each of the 3 cell types and they were allowed to differentiate or transdifferentiate for up to 3 weeks, using media conditions found in literature (such as, for example, B27 Supplement in DMEM-F12-Glutamax), supplemented with biologically active synthetic nanoparticle constructs. To examine cell differentiation, the identity of the cells were determined by immunostaining with cell-specific markers for iPSCs (e.g., Nestin, Msi1, Sox2), neurons (e.g., Dcx, Tuji, NeuN, and GAD65/67), astrocytes (e.g., GFAP, GS, and S100b), and oligodendrocytes (e.g., Olig2, PDGFRa, CC1, O4, and CNPase). In addition, PCR was performed on biologically active synthetic nanoparticle construct treated cells to measure ASCL1 expression, as well as neuronal marker expression, such as Tujl, NeuN, and Map2. Lastly, calcium imaging was used to determine whether the cells could generate calcium influxes.

Example B2.2

Investigation of Transplantation of Biologically Active Synthetic Nanoparticle Construct-Induced Functional Neurons into Mouse SCI Models After demonstrating the successful in vitro differentiation of functional neurons using the biologically active synthetic nanoparticle construct-ASCL1, an examination was conducted to determine whether biologically active synthetic nanoparticle construct-derived neurons could ameliorate behavioral and functional defects in an in vivo mouse model of SCI. To this end, green fluorescent protein (GFP) labeled IPSCs, fibroblasts, or astrocytes, in vitro transfected with biologically active synthetic nanoparticle construct, were transplanted into an animal model at different stages of differentiation (early, mid, and late-stage neuron differentiation). After transplanting these biologically active synthetic nanoparticle construct-derived neurons into the SCI mouse model, biologically active synthetic nanoparticle construct-derived neuron cell behaviors were evaluated, regarding survival, proliferation, differentiation, and integration into the host spinal cord. Previous transplantation studies have shown that cells in the neural progenitor stage had better functional and behavioral outcomes than mature neurons. Based on these studies, the in vivo function of early neuronal stage cells from biologically active synthetic nanoparticle construct-derived neurons was tested, as undifferentiated cells have a higher possibility of tumor formation, and late neuronal stage cells have extremely low survival. The stage of differentiation was determined using fluorescence activated cell sorting (FACS).

For transplantation into SCI mice models, established methods and protocols were utilized to provide anesthesia, transplant neurons, and administer proper supplements. After monitoring behavioral responses 1, 2, 4, and 6 weeks after transplantation, the mice were anesthetized terminally, and image capture equipment and analysis software were utilized to analyze phenotypic expression, morphological, and differentiation characteristics. Furthermore, cell survival and any teratoma formation were carefully monitored during the study. Immunofluorescent labeling and confocal microscopy was performed to determine co-expression of additional neuronal markers (e.g., DDC, DAT, and ViviAT2) and other phenotypic markers (e.g., 5-HT, DBH, AChE, DARP-32, GAB A, and GFAP). These experiments confirmed the differentiation and maturation of neuronal phenotypes in vivo. In addition to the above phenotypic gene expression, the study investigated whether these differentiated neurons exhibited mature neuronal morphology and synaptic integration into host spinal cord, by confocal microscopic analyses, using specific antibodies against synaptic marker proteins such as synaptophysin and synapsin. Electrophysiological recordings were conducted to determine the functional properties of these transplanted neurons. Based on these studies, the optimal conditions of the biologically active synthetic nanoparticle construct-induced neurons, such as the differentiation stage for transplantation, and number of cells to be grafted, were determined.

The results established the biologically active synthetic nanoparticle construct as a powerful, non-viral, and safe platform of cellular reprogramming at different stages of differentiation for the regeneration of spinal cord function and behavior, demonstrating treatment potential for SCI patients, and the clinical potential of the biologically active synthetic nanoparticle construct as a tool to safely modulate gene expression for stem cell-based therapies, as well as other neuro-degenerative medical applications. The experiments also demonstrated the utility of the biologically active synthetic nanoparticle construct for the personalized stem cell-based therapy of SCI and many other disorders. The data demonstrated the ability to i) engineer specific DNA binding motifs; ii) establish specific biologically active synthetic nanoparticle constructs for specific TFs (e,g, ASCL1); iii) successfully differentiate functional neurons from various cell lines; and (iv) successfully use transplantation of biologically active synthetic nanoparticle constructs to restore normal behavior, e,g, for SCI.

Example B3

Transplantation of Biologically Active Synthetic Nanoparticle Constructs into the Damaged Spinal Cord to Convert Astrocytes, Fibroblasts and Stem Cells into Functional Neurons:

While stem cell transplantation is an interesting approach for the treatment of spinal cord injury, the biologically active synthetic nanoparticle construct platform has the advantages of being both biocompatible and degradable in vivo. In addition, post-SCI glial cells and invading fibroblasts form the glial and fibrotic scar respectively. Studies have shown that both fibroblasts and astrocytes have the potential to be converted into neurons with mature morphology. Therefore, this study focused on the direct delivery of biologically active synthetic nanoparticle constructs into the injured spinal cord, to convert the local cells into functional neurons.

Rats were randomly divided into two groups: control (n=10) and with biologically active synthetic nanoparticle construct-ASCL1 treatments (each treatment n=10). Sprague-Dawley female rats were anesthetized with isoflurane (5% initially and 2% maintenance), shaved, and the skin on the back cleaned with betadine and alcohol wipes. Contusion of the rat spinal cord at the T13-L1 vertebral junction was be induced with a 10-gram weight, dropped from a height of 25 mm, onto the dural surface of the spinal cord, causing a moderately severe injury. Subcutaneous fat was placed on the dural surface, to retard adhesion of dura to surrounding tissues. The skin was closed with stainless steel clips. Contusion of the spinal cord generated severe hematoma inside the spinal cord, and any incision on dura resulted in the spinal cord tissue "mushrooming" out. This prevented any surgical manipulation inside the spinal cord, and thus restricted any material implantation during the acute phase. The biologically active synthetic nanoparticle construct-ASCL1 was injected at the subacute phase, 2 weeks after injury, when major inflammatory responses had subsided. Rats were anesthetized with isoflurane and the laminectomy site was re-exposed. The biologically active synthetic nanoparticle construct-ASCL1 was injected into the spinal cord (1-10 mg/kg starting with the optimized conditions from Example A, and further improved empirically). The skin was closed with stainless steel clips. One week after the SCI surgery, animals were divided into two groups with n=10 rats per group: (1) untreated and (2) biologically active synthetic nanoparticle construct-ASCL1, at 25 mm 10 g weight drop. As in Example B2, after monitoring behavioral responses 1, 2, 4, and 6 weeks after transplantation, the mice were anesthetized terminally, and image capture equipment and analysis software were utilized to analyze phenotypic expression, morphological, and differentiation characteristics. Immunofluorescent labeling and confocal microscopy was performed to determine co-expression of additional neuronal markers (e.g., DDC, DAT, and VMAT2) and other phenotypic markers (e.g., 5-HT, DBH, AChE, DARP-32, GABA, and GFAP). These experiments confirmed the differentiation and maturation of neuronal phenotypes in vivo. In addition to the above phenotypic gene expression, the study investigated whether these differentiated neurons exhibited mature neuronal morphology, and synaptic integration into the host spinal cord, by confocal microscopic analyses using specific antibodies against synaptic marker proteins such as synaptophysin and synapsin.

The experiments evaluated the biologically active synthetic nanoparticle construct for the personalized stem cell-based therapy of SCI and many other disorders. The study demonstrated the ability to i) engineer specific DNA binding motifs; ii) establish specific biologically active synthetic nanoparticle constructs for specific TFs (e.g. ASCL1); and iii) successfully differentiate functional neurons from NPSCs; and (iv) successfully use transplantation of biologically active synthetic nanoparticle constructs to restore normal behavior, e,g, for SCI.

It will be appreciated by those skilled in the art that changes could be made to the embodiments described above without departing from the broad inventive concept thereof. It is understood, therefore, that this invention is not limited to the particular embodiments or examples disclosed, but it is intended to cover modification that are within the spirit and scope of the present invention as defined by the appended claims.

What is claimed is:

1. A biologically active synthetic nanoparticle construct comprising a polypeptide-dendrimer nanoparticle, and a plurality of moieties attached to a surface of the polypeptide-dendrimer nanoparticle, wherein the moieties comprise:

i. a plurality of single copies of DNA binding domains, ii. a plurality of single copies of nuclear localization signals, and iii. a plurality of single copies of transcriptional domains, wherein the DNA binding domains are each individually covalently attached to the surface of the polypeptide-dendrimer nanoparticle, wherein the nuclear localization signals are each individually covalently attached to the surface of the polypeptide-dendrimer nanoparticle, and wherein the transcriptional domains are each individually covalently attached to the surface of the polypeptide-dendrimer nanoparticle.

2. The biologically active synthetic nanoparticle construct of claim 1 wherein:

i. X % of the moieties on the polypeptide-dendrimer nanoparticle are DNA binding domains, wherein X % ranges from 10 to 70%;

ii. Y % of the moieties on the polypeptide-dendrimer nanoparticle are transcriptional repression domains, wherein Y % ranges from 10 to 70%;

iii. Z % of the moieties on the polypeptide-dendrimer nanoparticle are nuclear localization signals, wherein Z % ranges from 10 to 70%; and iv. the sum of X, Y, and Z % is not greater than 100%.

3. The biologically active synthetic nanoparticle construct of claim 2, wherein Z % is at least 50%.

4. The biologically active synthetic nanoparticle construct of claim 1, wherein the moieties further comprise a plurality of at least one conjugant;

wherein W % of the moieties on the polypeptide-dendrimer nanoparticle are the conjugants, wherein W % ranges from 0 to 40%; and wherein the sum of W, X, Y and Z % is not greater than 100%.

5. The biologically active synthetic nanoparticle construct of claim 1 wherein the polypeptide-dendrimer nanoparticle comprises:

i. a hydrophobic core comprising a dendrimer, wherein the dendrimer comprises an amide linker and an amine functionalization suitable for N-carboxyanhydride polymerization;

ii. a hydrophobic inner shell comprising an inner shell polypeptide, wherein the hydrophobic inner shell at least partially surrounds the hydrophobic core; and iii. a hydrophilic outer shell comprising an outer shell polypeptide, wherein the hydrophilic outer shell at least partially surrounds the hydrophobic inner shell.

6. The biologically active synthetic nanoparticle construct of claim 5 wherein the dendrimer comprises a polyamidoamine.

7. The biologically active synthetic nanoparticle construct of claim 5 wherein the inner shell polypeptide comprises polymerized hydrophobic amino acids selected from the group consisting of glycine, alanine, valine, leucine, isoleucine, phenylalanine, methionine, tryptophan, cysteine, and a combination thereof.

8. The biologically active synthetic nanoparticle construct of claim 5 wherein the outer shell polypeptide comprises polymerized alpha amino acids.

9. The biologically active synthetic nanoparticle construct of claim 8 wherein the alpha amino acids are selected from the group consisting of lysine, glutamic acid, aspartic acid, and a combination thereof.

10. The biologically active synthetic nanoparticle construct of claim 5 wherein the outer shell polypeptide has an isoelectric point of from at least 6.5 to no more than 8.

11. The biologically active synthetic nanoparticle construct of claim 5, wherein the outer shell polypeptide comprises a functional group selected from the group consisting of an amine, a carboxyl, a phosphonate, a sulfonate, and a combination thereof.

12. The biologically active synthetic nanoparticle construct of claim 5, wherein the outer shell polypeptide has a functional group consisting of sulfosuccinimidyl 4-(N-maleimido-methyl)cyclohexane-1-carboxylate.

13. The biologically active synthetic nanoparticle construct of claim 1 wherein the polypeptide-dendrimer nanoparticle is loaded with at least one of, hydrophobic small molecules, oligonucleotides, and ions.

14. The biologically active synthetic nanoparticle construct of claim 13 wherein the ion is selected from the group consisting of gadolinium, manganese, rhenium, and a combination thereof.

15. The biologically active synthetic nanoparticle construct of claim 1 wherein the polypeptide-dendrimer nanoparticle is prepared by the process of:
  i. performing a Michael addition and amidation reaction between an amine and an acrylate to form a hydrophobic dendrimer core having an outer surface;
  ii. polymerizing a plurality of hydrophobic amino acids, by N-carboxyanhydride polymerization, in the presence of the hydrophobic dendrimer core, to form a hydrophobic polypeptide inner shell having an outer surface,
    wherein the hydrophobic polypeptide inner shell at least partially surrounds the outer surface of the hydrophobic core; and
  iii. polymerizing a plurality of hydrophilic alpha amino acids, by N-carboxyanhydride polymerization, in the presence of the hydrophilic inner shell, to form a hydrophilic polypeptide outer shell having an outer surface,
    wherein the hydrophilic polypeptide outer shell at least partially surrounds the outer surface of the hydrophobic inner shell.

16. The biologically active synthetic nanoparticle construct of claim 15, wherein the amine comprises tri(2-aminoethyl)amine, and the acrylate comprises methyl acrylate.

17. The biologically active synthetic nanoparticle construct of claim 1 wherein the DNA binding domain is selected from the group consisting of hairpin polyamides, zinc finger domains, triplex-forming oligonucleotides (TFOs), transcription activator-like effectors, oligonucleotide analogs, locked-nucleic acids, peptide nucleic acids, and a combination thereof.

18. The biologically active synthetic nanoparticle construct of claim 1,
  wherein the DNA binding domains are hairpin polyamides, and
  wherein the hairpin polyamides comprise at least one N-methyl-imidazole moiety or at least one N-methyl pyrrole moiety, or combinations thereof, arranged sequentially on the polyamide to bind a target gene.

19. The biologically active synthetic nanoparticle construct according to claim 1, wherein the transcriptional domains are transcriptional activation domains.

20. The biologically active synthetic nanoparticle construct according to claim 19, wherein the transcriptional activation domains are selected from the group consisting of peptoids, amphipathic isoxasolidine, wrenchnolol, amphipathic helix peptides and combinations thereof.

21. The biologically active synthetic nanoparticle construct according to claim 1, wherein the transcriptional domains consist of peptides.

22. The biologically active synthetic nanoparticle construct of claim 1 wherein the nuclear localization signals are derived from a SV-40 antigen, derived form an HIV-1 antigen, or derived from the group consisting of: TAT, Penetratin, MAP, Transportin/TP10, VP22, MPG, Pep1, pVEC, YTA2, YTA4, M918, CADY, and combinations thereof.

23. The biologically active synthetic nanoparticle construct according to claim 1, wherein the transcriptional domains are transcriptional repression domains.

* * * * *

UNITED STATES PATENT AND TRADEMARK OFFICE
CERTIFICATE OF CORRECTION

| | |
|---|---|
| PATENT NO. | : 11,306,326 B2 |
| APPLICATION NO. | : 16/437898 |
| DATED | : April 19, 2022 |
| INVENTOR(S) | : Ki-Bum Lee et al. |

Page 1 of 1

It is certified that error appears in the above-identified patent and that said Letters Patent is hereby corrected as shown below:

In the Specification

At Column 1, Line number 24 should read:
This invention was made with government support under grant number OD006462 awarded by the National Institutes of Health. The government has certain rights in the invention.

Signed and Sealed this
Sixteenth Day of April, 2024

Katherine Kelly Vidal
*Director of the United States Patent and Trademark Office*